US006995255B1

(12) United States Patent
Riley et al.

(10) Patent No.: US 6,995,255 B1
(45) Date of Patent: Feb. 7, 2006

(54) CELLULAR DELIVERY AGENT

(75) Inventors: Lee W. Riley, Berkeley, CA (US); Sangwei Lu, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 155 days.

(21) Appl. No.: 10/382,176

(22) Filed: Mar. 4, 2003

Related U.S. Application Data

(60) Provisional application No. 60/362,229, filed on Mar. 5, 2002.

(51) Int. Cl.
C07H 21/04 (2006.01)
C07H 21/02 (2006.01)
A61K 39/04 (2006.01)

(52) U.S. Cl. ............... 536/23.7; 424/9.1; 424/9.2; 424/234.1; 424/248.1; 435/41; 435/320.1; 435/440; 435/471; 536/23.1

(58) Field of Classification Search ........... 424/9.1, 424/9.2, 234.1, 248.1; 435/41, 320.1, 440, 435/471; 536/23.1, 23.7
See application file for complete search history.

(56) References Cited

U.S. PATENT DOCUMENTS

| 6,008,201 A | 12/1999 | Riley |
| 6,072,048 A | 6/2000 | Riley |
| 6,214,543 B1 | 4/2001 | Riley |
| 6,224,881 B1 | 5/2001 | Riley et al. |
| 2001/0019716 A1 | 9/2001 | Riley et al. |

OTHER PUBLICATIONS

Arruda, et al. (1992) "Cloning of a *Mycobacterium tuberculosis* Gene Necessary for Invasion of Cultured Epithelial Cells" *Abstracts of the 92nd General Meeting of the American Society for Microbiology—1992*: 41.
Arruda, et al. (1993) "Cloning of an *M. tuberculosis* DNA Fragment Associated with Entry and Survival Inside Cells" *Science* 261: 1454-1457.
Bliska, James B. et al. (1993) "Signal Transduction in the Mammalian Cell during Bacterial Attachment and Entry" *Cell* 73: 903-920.
Casali, Nicola et al. (2002) "Invasion Activity of a *Mycobacterium tuberculosis* Peptide Presented by the *Escherichia coli* AIDA Autotransporter" *Infection and Immunity* 70: 6846-6852.
Chitale, Sadhana et al. (2001) "Recombinant *Mycobacterium tuberculosis* protein associated with mammalian cell entry" *Cellular Microbiology* 3 (4): 247-254.
Cole, S. T. (1998) "Deciphering the biology of *Mycobacterium tuberculosis* from the complete genome sequence" *Nature* 393: 537-.
Hirsch, Christina S. et al. (1994) "Complement Receptor-Mediated Uptake and Tumor Necrosis Factor-α-Mediated Growth Inhibition of *Mycobacterium tuberculosis* by Human Alveolar Macrophages" *Journal of Immunology* 152: 743-753.
Horwitz, Marcus A. (1995) "Protective immunity against tuberculosis induced by vaccination with major extracellular proteins of *Mycobacterium tuberculosis*" *Proc. Natl. Acad. Sci. USA* 92: 1530-1534.
Isberg, Ralph R. and Stanley Falkow, (1985) "A single genetic locus encoded by *Yersinia pseudotuberculosis* permits invasion of cultured animal cells by *Escherichia coli* K-12" *Nature* 317: 262-264.
Lu, S. and L. W. Riley (1998) "A peptide from *Mycobacterium tuberculosis* Mediates Adhesion to and Uptake by Mammalian Cells" *ASM 98th General Meeting*, Atlanta Georgia: 70-71.

*Primary Examiner*—Rodney P. Swartz
(74) *Attorney, Agent, or Firm*—Morrison & Foerster LLP

(57) ABSTRACT

One aspect of the present invention relates to a nucleic acid construct which includes a first nucleic acid and a second nucleic acid operatively coupled to the first nucleic acid. The first nucleic acid molecule encodes a first peptide that has the sequence of InvX or another sequence incorporating the 58 amino acid cellular import region of Mce1A and confers on *Mycobacterium tuberculosis* an ability to enter mammalian cells. The second nucleic acid molecule encoding a second peptide. Expression of the nucleic acid construct produces a fusion protein comprising the first peptide coupled to the second peptide. The second peptide may be a therapeutic or a diagnostic peptide. An alternative embodiment of the nucleic acid construct includes the first nucleic acid and an insertion site suitable for incorporation of the second nucleic acid molecule into this version of the construct. The present invention further relates to the fusion protein per se, screening methods for identifying fusion proteins having a protective effect against a pathogen, and therapeutic fusion proteins.

16 Claims, 8 Drawing Sheets (a)  (b)

SEQUENCE LISTING

```
<160> NUMBER OF SEQ ID NOS: 10

<210> SEQ ID NO 1
<211> LENGTH: 1535
<212> TYPE: DNA
<213> ORGANISM: Mycobacterium tuberculosis

<400> SEQUENCE: 1
ggatcgaatt gctggccttt ggcgggcgat tcgtggagat cgcccgtaga aaggttcgcg      60
gacgccaagg ccgccgcaga ccgccataaa cgtagttgac caggtggtct tgactggggc     120
cggacaccga cgtgaacgag gcgacccgat ccgcgttaca tccacctgat tccggcaaat     180
gtgaacgccg acatcaaggc gaccacggtg ttcggcggta agtatgtgtc ggtgaccacg     240
ccgaaaaacc cgacaaagag gcggataacg ccaaaagacg tcatcgacgt acgtcggtg     300 accaccgaga tcaacacgtt gttccagacg ctcacctcga tcgccgagaa ggtggatccg     360
gtcaagctca acctgaccct gagcgcgcc gcggaggcgt tgaccgggct gggcgataag     420
ttcggcgagt cgatcgtcaa cgccaacacc gttctggatg acctcaattc gcggatgccg     480
cagtcgcgcc acgacattca gcaattggcg gctctgggcg acgtctacgc cgacgcggcg     540
ccggacctgt tcgactttct cgacagttcg gtgaccaccg cccgcaccat caatgcccag     600
caagcggaac tggattcggc gctgttggcg gcggccgggt tcggcaacac cacagccgat     660
gtcttcgacc gcggcgggcc gtatctgcag cgggggtcg ccgacctggt ccccaccgcc     720
accctgctcg acacttatac cccggaactg ttctgcacga tccgcaactt ctacgatgcc     780
gatcgacctg accgcggggc tgccgcatag gcccggagtg gttcgcgatc ggcgaggcgc     840
acgtcaaagt gattcgcgcc cttttttcgcc cacctgcccg ccgcggtgga tgtgtccacc     900
cgccaggccg ccgaagccga cctggccggc aaagccgctg aatatcgtcc cgacgagctg     960
gcccgctacg cccagcgggt catggactgg ctacacccg acggcgacct caccgacacc    1020
gaacgcgccc gcaaacgcgg catcaccctg agcaaccagc aatacgacgg catgtcacgg    1080
ctaagtggct acctgacccc ccaagcgcgg gccaccttg aagccgtgct agccaaactg    1140 gccgccccg gcgcgaccaa ccccgacgac cacacccgg tcatcgacac cacccccgat    1200
gcggccgcca tcgaccgcga cacccgcagc caagcccaac gcaaccacga cgggctgctg    1260
```

-continued

```
gccgggctgc gcgcgctgat ccgtcatcct gccatctcgg ccctcggcgc cgccaactcc      1320
aggtgctgtg cggtccacgc cgaacgcatg cacgcgatct cgaattggtt ggcaccgtat      1380
tcgggatgga actgctcgat agcgatgcct gctgccgttg ccgcggcgtt gacatcgcgg      1440
acgaacgcct cgtgctcgag caccccggcg acaccgtact gcgcccacag cgtcgaaggc      1500
agccgctggc cgtccgcgtc gaccaagagg aattc                                1535
```

<210> SEQ ID NO 2
<211> LENGTH: 507
<212> TYPE: PRT
<213> ORGANISM: Mycobacterium tuberculosis

<400> SEQUENCE: 2

```
Gly Ser Asn Cys Trp Pro Leu Ala Gly Asp Ser Trp Arg Ser Pro Val
 1               5                  10                  15

Gly Arg Phe Ala Asp Ala Lys Ala Ala Asp Arg His Lys Arg Ser
             20                  25                  30

Pro Gly Gly Leu Asp Trp Gly Arg Thr Pro Thr Thr Arg Arg Pro Asp
         35                  40                  45

Pro Arg Tyr Ile His Leu Ile Pro Ala Asn Val Asn Ala Asp Ile Lys
     50                  55                  60

Ala Thr Thr Val Phe Gly Gly Lys Tyr Val Ser Leu Thr Thr Pro Lys
 65                  70                  75                  80

Asn Pro Thr Lys Arg Arg Ile Thr Pro Lys Asp Val Ile Asp Val Arg
                 85                  90                  95

Ser Val Thr Thr Glu Ile Asn Thr Leu Phe Gln Thr Leu Thr Ser Ile
            100                 105                 110

Ala Glu Lys Val Asp Pro Val Lys Leu Asn Leu Thr Leu Ser Ala Ala
        115                 120                 125

Ala Glu Ala Leu Thr Gly Leu Gly Asp Lys Phe Gly Glu Ser Ile Val
    130                 135                 140

Asn Ala Asn Thr Val Leu Asp Asp Leu Asn Ser Arg Met Pro Gln Ser
145                 150                 155                 160

Arg His Asp Ile Gln Gln Leu Ala Ala Leu Gly Asp Val Tyr Ala Asp
                165                 170                 175

Ala Ala Pro Asp Leu Phe Asp Phe Leu Asp Ser Ser Val Thr Thr Ala
            180                 185                 190

Arg Thr Ile Asn Ala Gln Gln Ala Glu Leu Asp Ser Ala Leu Leu Ala
        195                 200                 205

Ala Ala Gly Phe Gly Asn Thr Thr Ala Asp Val Phe Asp Arg Gly Gly
    210                 215                 220

Pro Tyr Leu Gln Arg Gly Val Ala Asp Leu Val Pro Thr Ala Thr Leu
225                 230                 235                 240

Leu Asp Thr Tyr Ser Pro Glu Leu Phe Cys Thr Ile Arg Asn Phe Tyr
                245                 250                 255

Asp Ala Asp Arg Pro Asp Arg Gly Ala Ala Ala Arg Ser Gly Ser
            260                 265                 270

Arg Ser Ala Arg Arg Thr Ser Lys Phe Ala Pro Phe Ala His Leu
        275                 280                 285

Pro Ala Ala Val Asp Val Ser Thr Arg Gln Ala Ala Glu Ala Asp Leu
    290                 295                 300

Ala Gly Lys Ala Ala Gln Tyr Arg Pro Asp Glu Leu Ala Arg Tyr Ala
305                 310                 315                 320
```

```
                Gln Arg Val Met Asp Trp Leu His Pro Asp Gly Asp Leu Thr Asp Thr
                            325                 330                 335

Glu Arg Ala Arg Lys Arg Gly Ile Thr Leu Ser Asn Gln Gln Tyr Asp
                            340                 345                 350

Gly Met Ser Arg Leu Ser Gly Tyr Leu Thr Pro Gln Ala Arg Ala Thr
                                355                 360                 365

Phe Glu Ala Val Leu Ala Lys Leu Ala Ala Pro Gly Ala Thr Asn Pro
                370                 375                 380

Asp His Thr Pro Val Ile Asp Thr Thr Pro Asp Ala Ala Ile
            385                 390                 395                 400

Asp Arg Asp Thr Arg Ser Gln Ala Gln Arg Asn His Asp Gly Leu Leu
                            405                 410                 415

Ala Gly Leu Arg Ala Leu Ile Arg His Pro Ala Ile Ser Ala Leu Gly
                            420                 425                 430

Ala Ala Asn Ser Arg Cys Cys Ala Val His Ala Glu Arg Met His Ala
                            435                 440                 445

Ile Ser Asn Trp Leu Ala Pro Tyr Ser Gly Trp Asn Cys Ser Ile Ala
                            450                 455                 460

Met Pro Ala Ala Val Ala Ala Ala Leu Thr Ser Arg Thr Asn Ala Ser
                465                 470                 475                 480

Cys Ser Ser Thr Pro Ala Thr Pro Tyr Cys Ala His Ser Val Glu Gly
                                485                 490                 495

Ser Arg Trp Pro Ser Ala Ser Thr Lys Arg Asn
                            500                 505

<210> SEQ ID NO 3
<211> LENGTH: 66
<212> TYPE: DNA
<213> ORGANISM: Mycobacterium tuberculosis
<220> FEATURE:
<221> NAME/KEY: CDS
<222> LOCATION: (1)...(66)

<400> SEQUENCE: 3 aca aag agg cgg ata acg cca aaa gac gtc atc gac gta cgg tcg gtg         48
Thr Lys Arg Arg Ile Thr Pro Lys Asp Val Ile Asp Val Arg Ser Val
  1               5                  10                  15 acc acc gag atc aac acg                                                 66
Thr Thr Glu Ile Asn Thr
            20

<210> SEQ ID NO 4
<211> LENGTH: 22
<212> TYPE: PRT
<213> ORGANISM: Mycobacterium tuberculosis

<400> SEQUENCE: 4

Thr Lys Arg Arg Ile Thr Pro Lys Asp Val Ile Asp Val Arg Ser Val
  1               5                  10                  15

Thr Thr Glu Ile Asn Thr
            20

<210> SEQ ID NO 5
<211> LENGTH: 240
<212> TYPE: DNA
<213> ORGANISM: Mycobacterium tuberculosis
<220> FEATURE:
<221> NAME/KEY: CDS
<222> LOCATION: (1)...(216)
```

```
<400> SEQUENCE: 5 gtg aac gcc gac atc aag gcg acc acg gtg ttc ggc ggt aag tat gtg         48
Val Asn Ala Asp Ile Lys Ala Thr Thr Val Phe Gly Gly Lys Tyr Val
 1               5                  10                  15 tcg ttg acc acg ccg aaa aac ccg aca aag agg cgg ata acg cca aaa         96
Ser Leu Thr Thr Pro Lys Asn Pro Thr Lys Arg Arg Ile Thr Pro Lys
             20                  25                  30 gac gtc atc gac gta cgg tcg gtg acc acc gag atc aac acg ttg ttc        144
Asp Val Ile Asp Val Arg Ser Val Thr Thr Glu Ile Asn Thr Leu Phe
         35                  40                  45 cag acg ctc acc tcg atc gcc gag aag gtg gat ccg gtc aag ctc aac        192
Gln Thr Leu Thr Ser Ile Ala Glu Lys Val Asp Pro Val Lys Leu Asn
     50                  55                  60 ctg acc ctg agc gcg gcc gcg gag gcgttgaccg ggctgggcga taag             240
Leu Thr Leu Ser Ala Ala Ala Glu
 65                  70

<210> SEQ ID NO 6
<211> LENGTH: 72
<212> TYPE: PRT
<213> ORGANISM: Mycobacterium tuberculosis

<400> SEQUENCE: 6

Val Asn Ala Asp Ile Lys Ala Thr Thr Val Phe Gly Gly Lys Tyr Val
 1               5                  10                  15

Ser Leu Thr Thr Pro Lys Asn Pro Thr Lys Arg Arg Ile Thr Pro Lys
             20                  25                  30

Asp Val Ile Asp Val Arg Ser Val Thr Thr Glu Ile Asn Thr Leu Phe
         35                  40                  45

Gln Thr Leu Thr Ser Ile Ala Glu Lys Val Asp Pro Val Lys Leu Asn
     50                  55                  60

Leu Thr Leu Ser Ala Ala Ala Glu
 65                  70

<210> SEQ ID NO 7
<211> LENGTH: 174
<212> TYPE: DNA
<213> ORGANISM: Mycobacterium tuberculosis
<220> FEATURE:
<221> NAME/KEY: CDS
<222> LOCATION: (1)...(174)

<400> SEQUENCE: 7 gtg aac gcc gac atc aag gcg acc acg gtg ttc ggc ggt aag tat gtg         48
Val Asn Ala Asp Ile Lys Ala Thr Thr Val Phe Gly Gly Lys Tyr Val
 1               5                  10                  15 tcg ttg acc acg ccg aaa aac ccg aca aag agg cgg ata acg cca aaa         96
Ser Leu Thr Thr Pro Lys Asn Pro Thr Lys Arg Arg Ile Thr Pro Lys
             20                  25                  30 gac gtc atc gac gta cgg tcg gtg acc acc gag atc aac acg ttg ttc        144
Asp Val Ile Asp Val Arg Ser Val Thr Thr Glu Ile Asn Thr Leu Phe
         35                  40                  45 cag acg ctc acc tcg atc gcc gag aag gtg                                174
Gln Thr Leu Thr Ser Ile Ala Glu Lys Val
     50                  55

<210> SEQ ID NO 8
<211> LENGTH: 58
<212> TYPE: PRT
<213> ORGANISM: Mycobacterium tuberculosis
```

```
<400> SEQUENCE: 8

Val Asn Ala Asp Ile Lys Ala Thr Thr Val Phe Gly Gly Lys Tyr Val
 1               5                  10                  15

Ser Leu Thr Thr Pro Lys Asn Pro Thr Lys Arg Arg Ile Thr Pro Lys
                20                  25                  30

Asp Val Ile Asp Val Arg Ser Val Thr Thr Glu Ile Asn Thr Leu Phe
            35                  40                  45

Gln Thr Leu Thr Ser Ile Ala Glu Lys Val
     50                  55

<210> SEQ ID NO 9
<211> LENGTH: 180
<212> TYPE: DNA
<213> ORGANISM: Mycobacterium tuberculosis
<220> FEATURE:
<221> NAME/KEY: CDS
<222> LOCATION: (1)...(180)

<400> SEQUENCE: 9 gtg aac gcc gac atc aag gcg acc acg gtg ttc ggc ggt aag tat gtg       48
Val Asn Ala Asp Ile Lys Ala Thr Thr Val Phe Gly Gly Lys Tyr Val
 1               5                  10                  15 tcg ttg acc acg ccg aaa aac ccg aca aag agg cgg ata acg cca aaa       96
Ser Leu Thr Thr Pro Lys Asn Pro Thr Lys Arg Arg Ile Thr Pro Lys
                20                  25                  30 gac gtc atc gac gta cgg tcg gtg acc acc gag atc aac acg ttg ttc      144
Asp Val Ile Asp Val Arg Ser Val Thr Thr Glu Ile Asn Thr Leu Phe
            35                  40                  45 cag acg ctc acc tcg atc gcc gag aag gtg gat ccg                      180
Gln Thr Leu Thr Ser Ile Ala Glu Lys Val Asp Pro
     50                  55                  60

<210> SEQ ID NO 10
<211> LENGTH: 60
<212> TYPE: PRT
<213> ORGANISM: Mycobacterium tuberculosis

<400> SEQUENCE: 10

Val Asn Ala Asp Ile Lys Ala Thr Thr Val Phe Gly Gly Lys Tyr Val
 1               5                  10                  15

Ser Leu Thr Thr Pro Lys Asn Pro Thr Lys Arg Arg Ile Thr Pro Lys
                20                  25                  30

Asp Val Ile Asp Val Arg Ser Val Thr Thr Glu Ile Asn Thr Leu Phe
            35                  40                  45

Gln Thr Leu Thr Ser Ile Ala Glu Lys Val Asp Pro
     50                  55                  60
```

CELLULAR DELIVERY AGENT

CROSS-REFERENCE TO RELATED APPLICATIONS

This application claims priority to 60/362,229 filed on Mar. 5, 2002, which is hereby incorporated by reference in its entirety.

The present invention was developed with support under National Institutes of Health Grant NO: AI35266. The U.S. Government may have certain rights in this invention.

FIELD OF THE INVENTION

The present invention is in the field of biology. In particular, the present invention relates to *Mycobacterium tuberculosis* cell entry protein fusion polypeptides and the plasmid used to construct such polypeptides.

BACKGROUND OF THE INVENTION

The ability to deliver polypeptides into various compartments of mammalian cells has obvious advantages and a wide variety of medical applications. There are several methods currently in use to deliver proteins into cells. They include the use of delivery systems (vectors) that take advantage of attenuated infectious agents that retain the ability to enter mammalian cells (viruses, bacteria), biological agents such as liposomes or dendrimers, and mechanical methods, such as needle injection of proteins or DNA directly into muscle or subcutaneous tissue.

Infectious agents, especially viruses, are highly efficient in their delivery capacity, but are limited by the size or number of proteins that can be expressed by them inside cells. In the era of AIDS and wide use of immunosuppressive chemotherapeutic agents, there is always a concern in using infectious agents to deliver products for human use, even if they are attenuated. There is also the potential for these viral vectors to induce an adverse inflammatory response in a host receiving such vectors. Liposomal systems are still not highly efficient in their cell delivery capacity, and the mechanical methods are limited by the fact that the proteins or DNA must be delivered parenterally. Delivery of foreign DNA into cells to express it inside mammalian cells offers great promise, but its limitations are many. It has to rely on high-level expression of the plasmid inside cells for the proteins to be processed properly and presented effectively, and the protein that is expressed must not undergo post-translational modification by the mammalian cell protein modification systems.

The *Mycobacterium tuberculosis* cell entry protein (Mce1A) protein (SEQ ID NO:2) confers on *Mycobacterium tuberculosis* an ability to enter mammalian cells. This protein has been described in previous patents and patent applications, including U.S. Pat. Nos. 6,214,543, 6,008,201 6,072,048, 6,224,881, and U.S. Patent Application 2001/0019716, each of which are hereby incorporated by reference in their entirety. These patents teach that by non-covalently associating the Mce1A protein and fragments thereof with heterologous pharmaceutical agents or proteins, such agents can be introduced into cells.

While useful, previous methods facilitating cell entry of heterologous proteins and particles require that the Mce1A protein or Mce1A protein fragments be purified and then attached or associated with the pharmaceutical agent. Such attachment and association reactions suffer from numerous inefficiencies including reduced activity of the pharmaceutical agent resulting from the association and/or attachment reaction.

Recent results showed that a fragment of Mce1A covalently linked as a fusion protein facilitates cell surface adhesion, and not cell entry. Inv3 (SEQ ID NO:4), a 22 amino acid fragment of the *Mycobacterium* cell entry protein, was covalently linked to beta-galactosidase (β-gal) and green fluorescent protein (GFP) to form Inv3 fusion proteins (Lu and Riley, Abstracts of the 98$^{th}$ General Meeting of the American Society for Microbiology). The Inv3-β-gal fusion proteins associated with HeLa cells. In addition, Inv3-β-gal fusion proteins that were non-covalently associated with colloid gold particles did not facilitate efficient import of the colloid gold particles into the HeLa cells, particularly in comparison to fusion proteins of InvX (SEQ ID NO:6), a 72 amino acid fragment incorporating the amino acids of Inv3.

There is thus a tremendous need to improve the efficiency of the Mce1 protein fragments as a pharmaceutical delivery agents, particularly when covalently linked to pharmaceutical delivery agents as fusion proteins capable of cell import.

SUMMARY OF THE INVENTION

In order to meet these needs, the present invention is directed to Mce1A peptide fusion proteins, nucleic acids encoding the Mce1A peptide fusion proteins, vectors including plasmids containing the nucleic acids encoding the Mce1A peptide and uses thereof.

Fusion proteins of Inv3 (SEQ ID NO:4), a 22 amino acid sequence of Mce1A, adhere to mammalian cells, but do not gain entry to cells. Surprisingly, InvX (SEQ ID NO:6), a 72 amino acid sequence including Inv3, facilitates both adhesion and cell entry. Cell entry and import refers to traversal of the cell membrane. In one embodiment, the present invention is directed to a nucleic acid construct having a first nucleic acid molecule encoding a first peptide including the amino acid sequence of SEQ ID NO: 6, SEQ ID NO: 8, or SEQ ID NO: 10, and a second nucleic acid molecule encoding a second peptide. The second nucleic acid molecule is operatively coupled to the first nucleic acid molecule, wherein expression of the nucleic acid construct produces a fusion protein of the first peptide coupled to the second peptide. The second peptide is generally a therapeutic or a diagnostic peptide. The resulting fusion protein product 1) is noninfectious and nontoxic, 2) is highly efficient in its ability to deliver any protein or polypeptide of choice into cells, 3) offers flexibility of use in either a parental, oral, or aerosol delivery format, 4) is able to deliver polypeptides into either the phagosomal or cytoplasmic component of cells, 5) can be made inexpensively, 6) finds use as a therapeutic agent, a diagnostic agent and an experimental tool.

The nucleic acids of the invention may be cloned into an expression vector such as a plasmid. The expression vectors of the invention are capable of expressing heterologous peptides in fusion with Mce1a peptides which confer on *Mycobacterium tuberculosis* an ability to enter mammalian cells.

The present invention is further directed to a host cell transformed with vectors containing the nucleic acid constructs of the invention. The present invention is further directed to a method of producing a fusion protein by providing the host cells of the invention expressing a fusion protein from the host cell, wherein the fusion protein includes a first protein and the second protein is operatively coupled to the first protein. The second peptide is generally a therapeutic or diagnostic peptide. The host cells may be bacterial, yeast, insect, fish or mammalian cells.

The present invention is further directed to a fusion protein having a first peptide including the amino acid sequence of SEQ ID NO: 6, SEQ ID NO: 8, or SEQ ID NO: 10, and a second peptide operatively coupled to the first peptide. The second peptide may be a diagnostic or a therapeutic peptide.

The present invention is further directed to a pharmaceutical composition including the fusion protein of the invention and a pharmaceutically acceptable carrier.

The present invention is further directed to a screening method for identifying antipathogenic fusion proteins. In one format of the method of the invention, a plurality of first different nucleic acid constructs including a first nucleic acid molecule encoding a first peptide including the amino acid sequence of SEQ ID NO: 6, SEQ ID NO: 8, or SEQ ID NO: 10, and a plurality of different second nucleic acid molecules each encoding a different second peptide are provided. Each of the second nucleic acid molecules are operatively coupled to the first nucleic acid molecule, wherein expression of each of the plurality of the first nucleic acid constructs produces a first different fusion protein including the first peptide coupled to one of the second peptides. Next, a plurality of homogeneous host cells are transformed with one of the plurality of first different nucleic acid constructs. Next, the plurality of first different fusion proteins are expressed with the plurality of host cells. Next, an animal is vaccinated with one of the first different fusion proteins and the vaccinated animal is challenged with a pathogen. Finally, it is determined which of the different first fusion peptides have an antipathogenic effect.

The method of the invention may further include subdividing the second nucleic acid molecules used to produce the first antipathogenic fusion proteins to form second nucleic acid molecule fragments; and providing a plurality of second different nucleic acid constructs including a first nucleic acid molecule encoding a first peptide, and a plurality of different second nucleic acid molecule fragments each encoding a different second protein fragment. Each of the different second nucleic acid molecule fragments individually is operatively coupled to the first nucleic acid molecule, wherein expression of each of the plurality of the second nucleic acid constructs produces a second different fusion protein including the first protein coupled to one of the different second protein fragments. Next, a plurality of homogeneous host cells are provided. Next, each of the plurality of host cells are provided with one of the plurality of second different nucleic acid constructs. The plurality of second different fusion proteins are expressed with the plurality of host cells. Next, an animal is vaccinated with one of the second different fusion proteins. The vaccinated animal is then challenged with the pathogen. Finally, it is determined which of the different second fusion proteins have antipathogenic activity.

The fusion proteins of the invention can also be utilized to 1) characterize antigens; 2) treat cancerous conditions; 3) treat infectious diseases; 4) screen fusion proteins for anti-pathogen activity; 5) identify vaccine candidates that can elicit cell mediated immune response against pathogens and tumor cells, 6) screen a genome of a pathogen for immunodominant and/or immunoprotective peptide sequences, and 7) deliver bioactive polypeptides (drugs, transcription factors, and other cell signal transducing factors).

In another aspect, the present invention is directed to a method of targeting a peptide for cell entry by making a fusion peptide and administering the fusion protein to a cell.

In another aspect, the present invention is directed to plasmids used for making the proteins and fusion proteins. In one variation, the plasmid includes SEQ ID NO:3. SEQ ID NO:3 may be placed downstream of a poly-histidine tag. SEQ ID NO:3 may also be operably linked to the sequence encoding β-galactosidase. The plasmid may be pInv, or pInvLZ. In another aspect, the plasmid may comprise SEQ ID NO:5. The plasmid may be operably linked to the sequence encoding AIDA. The sequence may be pMK100.

BRIEF DESCRIPTION OF THE SEQUENCE LISTING

Figure 1:
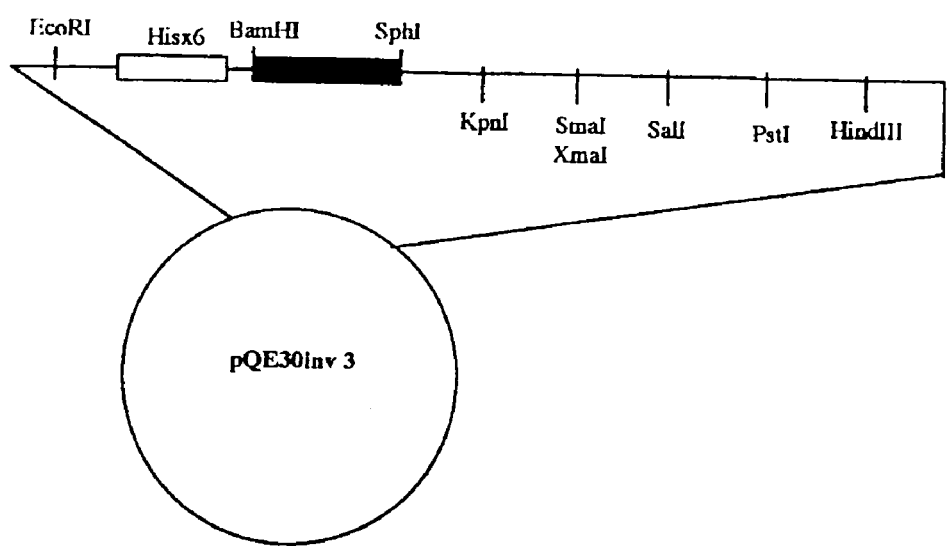
FIG. 1 shows a diagram of pInv3 plasmid constructed from an expression plasmid pQE30. The DNA fragment encoding the Inv3 peptide sequence was cloned into the BamH1/Sph1 restriction site of the plasmid, downstream of a polyhistidine-encoding sequence. The presence of a polycloning site downstream of the inv3 sequence offers versatility in cloning a variety of coding sequences. The cloned coding sequence will be expressed as a fusion protein with a Hisx6 and Inv3 at the N-terminus. The Hisx6 at the N-terminus will facilitate protein purification using a nickel column.

SEQ ID NO:1 is a nucleotide sequence encoding the full length Mce1A that promotes uptake of *E. coli* into mammalian cells.

SEQ ID NO:2 is the full length amino acid sequence of the full length Mce1A that promotes uptake of *E. coli* into mammalian cells.

SEQ ID NO:3 is a nucleotide sequence encoding the Inv3 peptide.

SEQ ID NO:4 is the amino acid sequence of the Inv3 peptide.

SEQ ID NO:5 is a nucleotide sequence encoding the InvX peptide.

SEQ ID NO:6 is the amino acid sequence of the InvX peptide.

SEQ ID NO:7 is a nucleotide sequence encoding the 58 amino acid region of Mce1A that facilitates uptake of Mce1A by mammalian cells.

SEQ ID NO:8 is the 58 amino acid active region of Mce1A responsible for cell entry.

SEQ ID NO:9 is a nucleotide sequence encoding a 60 amino acid peptide that includes the active region of McceA1.

SEQ ID NO:10 is the a 60 amino acid peptide including the active region of McceA1.

DETAILED DESCRIPTION OF THE INVENTION

Definitions

In order to more completely understand the invention, the following definitions are provided.

Fusion Proteins: A fusion protein is a fusion or linkage of two or more different peptides. The linked peptides may be joined or linked by a linker peptide. Fusion proteins generally have one or more copies of an active portion of a first polypeptide linked at the amino(N-) or carboxy (C-) terminus to all or a active portion of a second polypeptide. The term "fusion protein" as used herein refers to a C-terminal to N-terminal fusion of a first protein and a second protein where one of the proteins is the Mce1A protein or an active fragment thereof and the other protein is generally a therapeutic or diagnostic protein. The fusion proteins of the present invention include constructs in which the C-terminal portion of the first protein is fused to the N-terminal portion of the second, and also constructs in which the C-terminal portion of the second protein is fused to the N-terminal portion of the first. In the invention, the Mce1A protein or active fragment thereof and the therapeutic or diagnostic protein can be placed at either the N-terminus or the C-terminus of the fusion protein. The Mce1 A protein or active fragment thereof can be supplied in multiple copies.

Therapeutic Peptides: Therapeutic Peptides are polypeptides with 3 or more amino acids which have therapeutic activity. Exemplary, but not limited examples of therapeutic peptides include those peptides described in PCT Publication WO/0069900 which is hereby incorporated by reference. Peptides of particular interest include peptide antibiotics, anti-neoplastic agents, cell cycle regulating peptides and other cell transduction regulating peptides. Of particular interest are polypeptides such as insulin to correct hyperglycemia, tumor suppressor proteins such as p53 and pRB to correct mutations that generate tumor cells, small GTPases to induce a desired cell signal transduction, HIV-protease-activated caspases to induce apoptosis in HIV-infected cells, and vaccine candidates to elicit cell-mediated immune response.

Diagnostic Peptides: Diagnostic peptides are polypeptides with 3 or more amino acids which have diagnostic activity. Exemplary, but not limited, examples of peptides with diagnostic activity include those available from Peninsula Labs, polypeptides that can be labeled with fluorophors to stain intracellular structures, or polypeptides that can be cross-linked to oligonucleotides or molecular beacons to facilitate in-situ hybridization or PCR assays.

Linker Peptide: Linker peptides are short peptides which link two peptides in a fusion protein. Linker peptides generally have random coil structures. Linker peptides are designed to maintain the activity of the two linked peptides. In particular, the linker peptide may be designed so as not to interrupt the normal fold of the protein or peptide fragment thereof and the diagnostic or therapeutic peptide forming the fusion protein. Linker peptides can consist of any amino acid in a variety of combinations of various lengths. A preferred linker consists of eight amino acids rich in glycine and proline. Glycine and proline residues are utilized because they are known to disrupt protein secondary structure. Disruption of protein secondary structure in a fusion protein can serve to keep the proteins active while maintaining the peptides at a short distance from each other. This separation of the two peptides can help ensure correct folding of the individual peptides as well as the retention of native function.

Fusion Proteins

The ability to deliver polypeptides into mammalian cells has obvious advantages and a wide variety of medical applications. Several methods of introducing polypeptides to mammalian cells have been developed, but lack the ability to target mammalian cells directly. Delivering a fusion protein including an amino acid sequence capable of cell adherence and/or import and an amino acid sequence that otherwise cannot adhere to and/or import into the cell are thus desirable.

The present invention is thus directed to a nucleic acid construct having a first nucleic acid molecule encoding a first protein which confers on *Mycobacterium tuberculosis* an ability to enter mammalian cells and a second nucleic acid molecule encoding a second protein, the second nucleic acid molecule is operatively coupled to the first nucleic acid molecule, wherein expression of the nucleic acid construct produces a fusion protein of the first protein coupled to the second protein. The full length nucleotide sequence encoding Mce1A is depicted in SEQ ID NO:1. The full length amino acid sequence of Mce1A is depicted in SEQ ID NO:2.

In particular, the first protein may be a 72 amino acid fragment of Mce1A named InvX (SEQ ID NO:6). The second protein is generally a therapeutic or a diagnostic protein. A DNA molecule encoding InvX is defined by sequence of SEQ ID NO: 5:

```
GTGAACGCCG ACATCAAGGC GACCACGGTG TTCGGCGGTA AGTATGTGTC GTTGACCACG      60

CCGAAAAACC CGACAAAGAG GCGGATAACG CCAAAAGACG TCATCGACGT ACGGTCGGTG     120

ACCACCGAGA TCAACACGTT GTTCCAGACG CTCACCTCGA TCGCCGAGAA GGTGGATCCG     180

GTCAAGCTCA ACCTGACCCT GAGCGCGGCC GCGGAG                               216
```

The DNA taught by SEQ ID NO:5 encodes the InvX peptide (SEQ ID NO:6):

```
Val Asn Ala Asp Ile Lys Ala Thr Thr Val Phe Gly Gly Lys Tyr Val
1               5                   10                  15

Ser Leu Thr Thr Pro Lys Asn Pro Thr Lys Arg Arg Ile Thr Pro Lys
                20              25                  30

Asp Val Ile Asp Val Arg Ser Val Thr Thr Glu Ile Asn Thr Leu Phe
            35              40              45

Gln Thr Leu Thr Ser Ile Ala Glu Lys Val Asp Pro Val Lys Leu Asn
    50              55              60

Leu Thr Leu Ser Ala Ala Ala Glu
65              70      72
```

As detailed in the examples, Inv3 fusion proteins are unable to gain entry to the cells. HeLa cells incubated with Inv-3-β-gal showed prominent staining for β-gal activity on the cell surface, but failed to show cell import. Moreover, analysis of import into HeLa cells by colloid gold particles coated in, and non-covalently associated with, purified Inv3-β-gal, failed to consistently facilitate import of intracellular gold particles above the background level. Cellular import activity of the gold particles by Inv3-β-gal was less than that of Inv3 peptide alone, indicating that Inv3 fusion proteins are less capable of facilitating cell import.

Surprisingly, unlike Inv3 fusion proteins, fusion proteins of 72 amino acid InvX mediate both adhesion to and import into mammalian cells. When expressed in *E. coli*, InvX mediated adhesion of *E. coli* to HeLa cells. Further, expression of fusion proteins including InvX was sufficient to mediate import of the *E. coli* by HeLa cells.

InvX contains a 58 amino acid region of the Mce1A protein identified as promoting import of *E. coli*. The improved activity of InvX fusion proteins over Inv3 fusion proteins extends to other fragments of InvX that contain the 58 amino acid region.

An example of a DNA molecule encoding the 58 amino acid region is depicted as the sequence of SEQ ID NO: 7:

```
GTGAACGCCG ACATCAAGGC GACCACGGTG TTCGGCGGTA AGTATGTGTC GTTGACCACG     60

CCGAAAAACC CGACAAAGAG GCGGATAACG CCAAAAGACG TCATCGACGT ACGGTCGGTG    120

ACCACCGAGA TCAACACGTT GTTCCAGACG CTCACCTCGA TCGCCGAGAA GGTG          174
```

The nucleotide sequence corresponding to SEQ ID NO: 7 encodes the peptide having the following amino acid (SEQ ID NO: 8):

```
Val Asn Ala Asp Ile Lys Ala Thr Thr Val Phe Gly Gly Lys Tyr Val
1               5                   10                  15

Ser Leu Thr Thr Pro Lys Asn Pro Thr Lys Arg Arg Ile Thr Pro Lys
            20                  25                  30

Asp Val Ile Asp Val Arg Ser Val Thr Thr Glu Ile Asn Thr Leu Phe
        35                  40                  45

Gln Thr Leu Thr Ser Ile Ala Glu Lys Val
    50                  55          58
```

Another example of a fusion protein containing the 58 amino acid region is a fusion protein including a 60 amino acid sequence. An example of a DNA molecule encoding the 60 amino acid sequence is the DNA sequence of SEQ ID NO: 9:

```
GTGAACGCCG ACATCAAGGC GACCACGGTG TTCGGCGGTA AGTATGTGTC GTTGACCACG      60

CCGAAAAACC CGACAAAGAG GCGGATAACG CCAAAAGACG TCATCGACGT ACGGTCGGTG     120

ACCACCGAGA TCAACACGTT GTTCCAGACG CTCACCTCGA TCGCCGAGAA GGTGGATCCG     180
```

The 60 amino acid peptide has the amino acid sequence (SEQ ID NO: 10):

```
Val Asn Ala Asp Ile Lys Ala Thr Thr Val Phe Gly Gly Lys Tyr Val
1               5                   10                  15

Ser Leu Thr Thr Pro Lys Asn Pro Thr Lys Arg Arg Ile Thr Pro Lys
            20                  25                  30

Asp Val Ile Asp Val Arg Ser Val Thr Thr Glu Ile Asn Thr Leu Phe
        35                  40                  45

Gln Thr Leu Thr Ser Ile Ala Glu Lys Val Asp Pro
    50                  55                  60
```

Fusion proteins are constructed by using appropriate restriction sites, revealed by inspection of the DNA molecule's sequence, to: (i) insert an interposon (Felly, et al., "Interposon Mutagenesis of Soil and Water Bacteria: A Family of DNA Fragments Designed for in vitro Insertion Mutagenesis of Gram-negative Bacteria," Gene 52:147-15 (1987), which is hereby incorporated by reference) such that truncated forms of the polypeptides or proteins of the present invention, that lack various amounts of the C-terminus, can be produced or (ii) delete various internal portions of the protein. Alternatively, the sequence can be used to amplify any portion of the coding region, such that it can be cloned into a vector supplying both transcription and translation start signals.

Variant DNA Molecules

DNA encoding fusion proteins that include InvX or other peptides containing the 58 amino acid region, as well as the DNA encoding the therapeutic and diagnostic peptides of the invention and active fragments thereof, can be obtained as described herein, or alternatively, can be any oligodeoxynucleotide sequence having all or a portion of a sequence represented herein, or their functional equivalents so long as they confer cell import capability. Such sequences may be substantially identical to those described herein. Generally, these DNA sequences will hybridize under high stringency conditions. Such oligodeoxynucleotide sequences can be produced chemically or mechanically, using known techniques.

The following terms are used to describe the sequence relationships between two or more nucleic acids or polynucleotides: (a) "reference sequence", (b)"comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller, 1988; the local homology algorithm of Smith et al. 1981; the homology alignment algorithm of Needleman and Wunsch 1970; the search-for-similarity-method of Pearson and Lipman 1988; the algorithm of Karlin and Altschul, 1990, modified as in Karlin and Altschul, 1993.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. 1988; Higgins et al. 1989; Corpet et al. 1988; Huang et al. 1992; and Pearson et al. 1994. The ALIGN program is based on the algorithm of Myers and Miller, supra. The BLAST programs of Altschul et al., 1990, are based on the algorithm of Karlin and Altschul supra.

Software for performing BLAST analyses is publicly available through the National Center for Biotechnology Information (NCBI) at the NCBI web site. This algorithm involves first identifying high scoring sequence pairs (HSPs) by identifying short words of length W in the query sequence, which either match or satisfy some positivevalued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences (see, e.g., Karlin & Altschul (1993). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al. 1997. Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g. BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=-4, and a comparison of both strands. For amino acid sequences, the BLASTP program uses as defaults a wordlength (W) of 3, an expectation (E) of 10, and the BLOSUM62 scoring matrix (see Henikoff & Henikoff, 1989). See the web site located at ncbi.n1m.nih.gov. Alignment may also be performed manually by inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, more preferably at least 80%, 90%, and most preferably at least 95%.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acID.

(e)(ii) The term "substantial identity" in the context of a peptide indicates that a peptide comprises a sequence with at least 70%, 71%, 72%, 73%, 74%, 75%, 76%, 77%, 78%, or 79%, preferably 80%, 81%, 82%, 83%, 84%, 85%, 86%, 87%, 88%, or 89%, more preferably at least 90%, 91%, 92%, 93%, or 94%, or even more preferably, 95%, 96%, 97%, 98% or 99%, sequence identity to the reference sequence over a specified comparison window. Preferably, optimal alignment is conducted using the homology alignment algorithm of Needleman and Wunsch (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridization are sequence dependent, and are different under different environmental parameters. The $T_m$ is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA—DNA hybrids, the $T_m$ can be approximated from the equation of Meinkoth and Wahl, 1984; $T_m$81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point for the specific sequence and its complement at a defined ionic strength and pH. However, severely stringent conditions can utilize a hybridization and/or wash at 1, 2, 3, or 4° C. lower than the thermal melting point I; moderately stringent conditions can utilize a hybridization and/or wash at 6, 7, 8, 9, or 10° C. lower than the thermal melting point I; low stringency conditions can utilize a hybridization and/or wash at 11, 12, 13, 14, 15, or 20° C. lower than the thermal melting point I. Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. An extensive guide to the hybridization of nucleic acids is found in Tijssen, 1993. Generally, highly stringent hybridization and wash conditions are selected to be about 5° C. lower than the thermal melting point $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4–6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long robes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0. 1×SSC at 60 to 65° C. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

The following are examples of sets of hybridization/wash conditions that may be used to clone orthologous nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M $NaPO_4$, 1 mM EDTA at 50° C. with washing in 2×SSC, 0.1% SDS at 50° C., more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.

Peptide Variants

Peptide variants are peptides with sequences different than that of the naturally occurring Mce1A peptide sequences and different than the therapeutic and diagnostic peptides of the fusion proteins of the invention while still retaining the activity of the peptides. In addition to peptide variants, it may be advantageous to modify the peptides in order to impose a conformational restraint upon them. This might be useful, for example, to mimic a naturally-occurring onformation of the peptide in the context of the native protein in order to optimize the activities of the peptides.

Modified peptides are referred to herein as "peptide analogs". The term "peptide analog" extends to any functional chemical equivalent of a peptide characterized by its increased stability and/or efficacy and immunogenicity in vivo or in vitro in respect of the practice of the invention. The term "peptide analog" is also used herein to the extent of any amino acid derivative of the peptides as described herein. Peptide analogs contemplated herein are produced by procedures that include, but are not limited to, modifications to side chains, incorporation of unnatural amino acids and/or their derivatives during peptide synthesis and the use of cross-linkers and other methods which impose conformational constraint on the peptides or their analogs.

It will be apparent that the peptides employed herein as fusion proteins can be modified in a variety of different ways without significantly affecting the functionally important immunogenic behavior thereof. Possible modifications to the peptide sequence may include the following:

One or more individual amino acids can be substituted by amino acids having comparable or similar properties, thus:

V may be substituted by I;

T may be substituted by S;

K may be substituted by R; or

L may be substituted by I, V, or M.

One or more of the amino acids of the peptides of the invention can be replaced by a "retro-inverso" amino acid, i.e., a bifunctional amine having a functional group corresponding to an amino acid, as discussed in published International application WO 91/13909, which is hereby incorporated by reference.

One or more amino acids can be deleted.

Structural analogs mimicking the 3-dimensional structure of the peptide can be used in place of the peptide.

Examples of side chain modifications contemplated by the present invention include modification of amino groups, such as by reductive alkylation by reaction with an aldehyde followed by reduction with NaBH; amidation with methylacetimidate; acetylation with acetic anhydride; carbamylation of amino groups with 2, 4, 6, trinitrobenzene sulfonic acid (TNBS); alkylation of amino groups with succinic anhydride and tetrahydrophthalic anhydride; and pyridoxylation of lysine with pyridoxal-5'-phosphate followed by reduction with NaBH$_4$.

The guanidino group of arginine residues may be modified by the formation of heterocyclic condensation products with reagents, such as 2,3-butanedione, phenylglyoxal and glyoxal.

The carboxyl group may be modified by carbodiimide activation via o-acylisourea formation followed by subsequent derivatisation, for example, to a corresponding amide.

Sulfhydryl groups may be modified by methods, such as carboxymethylation with iodoacetic acid or iodoacetamide; performic acid oxidation to cysteic acid; formation of disulphides mixed with other thiol compounds, reaction with maleimide; maleic anhydride or other substituted maeimide; formation of mercurial derivatives using 4-chloromercuribenzoate, 4-chloromercuriphenylsulfonic acid, phenylmercury chloride, 2-chloromercuric-4-nitrophenol and other mercurials; carbamylation with cyanate at alkaline pH.

Tryptophan residues may be modified by, for example, oxidation with N-bromosuccinimide or alkylation of the indole ring with 2-hydroxy-5-nitrobenzyl bromide or sulphonyl halides. Tyrosine residues may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids.

Further, the peptides of the present invention may be lipidated with, for example, cholesterol or palmitate to incorporate it into cationic liposomes.

Recombinant Expression Systems

Any one of the nucleic acid constructs of the present invention can be incorporated in expression systems using conventional recombinant DNA technology. Generally, this involves inserting the selected DNA molecule into an vector such as a plasmid to which that DNA molecule encoding the fusion protein is heterologous (i.e. not normally present). The vectors are then introduced into a cellular host to form the expression system. Such cells may be bacterial, yeast, insect, plant, algae or viral. The heterologous DNA molecule is inserted into a vector in proper orientation and correct reading frame. The expression vectors may include nucleic acid sequences encoding a tag polypeptide. Such tag polypeptides include poly-histidine (poly-his) or poly-histidine-glycine (poly-his-gly) tags, flu HA tag polypeptides, c-myc tags, Herpes Simplex virus glycoprotein D (gD) tags and Flag-peptides. Such cloning sites may be downstream, upstream or within the coding region of the fusion peptides. The tag polypeptide permits the expression of a fusion protein with a tag polypeptide that permits ready purification of the protein. For example, with a hexa-histidine sequence, the protein can be readily purified using a nickel resin column. The vector contains the necessary elements for the transcription and translation of the inserted protein-coding sequences.

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

Recombinant genes may also be introduced into viruses, such as vaccina virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK+/−or KS+/−(see "Stratagene Cloning Systems" Catalog (1993) from Stratagene, La Jolla, Calif., which is hereby incorporated by reference), pQE, pIH821, pGEX, pET series (see F. W. Studier et. al., "Use of T7 RNA Polymerase to Direct Expression of Cloned Genes," Gene Expression Technology vol. 185 (1990), which is hereby incorporated by reference) and any derivatives thereof. Recombinant molecules can be introduced into cells via transformation, particularly transduction, conjugation, mobilization, or electroporation. The DNA sequences are cloned into the vector using standard cloning procedures in the art, as described by Maniatis et al., *Molecular Cloning: A Laboratory Manual*, Cold Springs Laboratory, Cold Springs Harbor, N.Y. (1982), which is hereby incorporated by reference.

A variety of host-vector systems may be utilized to express the fusion protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus). The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of fusion protein DNA is dependent upon the presence of a promoter which is a DNA sequence that directs the binding of RNA polymerase and thereby promotes mRNA synthesis. The DNA sequences of eucaryotic promoters differ from those of procaryotic promoters. Furthermore, eucaryotic promoters and accompanying genetic signals may not be recognized in or may not function in a procaryotic system, and, further, procaryotic promoters are not recognized and do not function in eucaryotic cells.

Similarly, translation of mRNA in prokaryotes depends upon the presence of the proper procaryotic signals which differ from those of eukaryotes. Efficient translation of mRNA in prokaryotes requires a ribosome binding site called the Shine-Dalgarno (SD) sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which is hereby incorporated by reference.

Promoters vary in their "strength" (i.e. their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the T7 phage promoter, lac promotor, trp promotor, recA promotor, ribosomal RNA promotor, the $P_R$ and $P_L$ promoters of coliphage lambda and others, including but not limited, to lacJV5, ompF, bla, Ipp, and the like, may be used to direct high levels of transcription of adjacent DNA segments. Additionally, a hybrid trp-lacUV5 (tac) promotor or other *E. coli* promoters produced by recombinant DNA or other synthetic DNA techniques may be used to provide for transcription of the inserted gene.

Bacterial host cell strains and expression vectors may be chosen which inhibit the action of the promotor unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promotor, may also contain any combination of various "strong" transcription and/or translation initiation signals. For instance, efficient translation in *E. coli* requires a Shine-Dalgarno (SD) sequence about 7–9 bases 5' to the initiation codon (ATG) to provide a ribosome binding site. Thus, any SD-ATG combination that can be utilized by host cell ribosomes may be employed. Additionally, any SD-ATG combination produced by recombinant DNA or other techniques involving incorporation of synthetic nucleotides may be used.

Once the desired nucleic acid construct has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, and the like.

Peptides can also be constructed synthetically as an alternative to recombinant formation.

Purification of Fusion Proteins

The peptides, proteins, or polypeptides of the present invention are preferably produced in purified form by conventional techniques.

To isolate the proteins, the host cell carrying recombinant DNA encoding a fusion protein is propagated, homogenized, and the homogenate is centrifuged to remove host debris. The supernatant may be subjected to sequential ammonium sulfate precipitation. The fraction containing the proteins of the present invention can be subjected to gel filtration in an appropriately sized dextran or polyacrylamide column to separate the proteins. If necessary, the protein fraction may be further purified by other chromatography, such as by HPLC affinity chromatography. Alternatively, affinity chromatography such as nickel chromatography or antibody chromatography may be utilized to purify the proteins using tag sequences.

Uses of the Fusion Proteins of the Invention

The fusion proteins of the invention can be imported into mammalian cells. This expression system, therefore, can be used for the following exemplary but not limiting applications: 1) screening fusion proteins for anti-pathogen activity; 2) identifying new vaccine candidates that can elicit cell mediated immune response against pathogens and tumor cells; 3) screening a genome of a pathogen for immunodominant and/or immunoprotective peptide sequences, 4) treatment of cancerous conditions; 5) treating pathogenic diseases and 6) delivering bioactive polypeptides (drugs, transcription factors, and other cell signal transducing factors).

1) Screening Fusion Proteins for Anti-Pathogen Activity

Another aspect of the present invention relates to a screening method for identifying fusion proteins having an immune protective effect against a pathogen. Such pathogens include but are not limited to obligate and facultative intracellular pathogens, such as pathogenic viruses of important human and animal diseases (including but not limited to HIV, HCV, HBV, influenza, HSV, CMV, HPV); bacterial pathogens including *Chlamydiae, Rickettsia, Salmonella, Shigella, Listeria, Yersinia, Mycobacterium tuberculosis,* and *Mycobacterium leprae*; and parasitic organisms, such as *Leishmania*. This method includes providing multiple different fusion protein nucleic acid constructs and transforming host cells with the nucleic acid constructs. The fusion proteins produced from the nucleic acid constructs are used to vaccinate an animal which is then challenged with the pathogen. As a result of such challenges, it is determined which of the different fusion proteins have a protective effect against the pathogen.

Once such effective fusion proteins are identified, subportions of the nucleic acids encoding those the second proteins of the fusion protein are identified. This involves subdividing the second nucleic acid molecules within the nucleic acid constructs encoding the fusion proteins which were effective as a vaccine to form additional nucleic acid molecule fragments. Multiple different nucleic acid constructs, each of which includes InvX or another peptide incorporating the 58 amino acid import region of Mce1A, and one of a plurality of different second nucleic acid molecule fragments each encoding a different second protein fragment, are then produced. Each of the different second nucleic acid molecule fragments are operatively coupled to the first nucleic acid molecule so that expression of each of the multiple second nucleic acid constructs produce a second different fusion protein. The fusion protein thus includes InvX or another peptide incorporating the 58 amino acid import region of Mce1A, coupled to one of the different second protein fragments.

Multiple homogeneous host cells are then provided and transformed with one of the plurality of second different nucleic acid constructs. The plurality of second different fusion proteins are expressed and used to vaccinate an animal. The vaccinated animal is then challenged with the pathogen and it is determined which of the different second fusion proteins has a protective effect against the pathogen.

This procedure of repeatedly determining which constructs can produce fusion proteins that are effective as vaccines and, then, reducing the size of the second nucleic acid molecule in identified constructs can be repeated until a fusion protein of the desired size is found.

In carrying out the screening procedure of the present invention, the second nucleic acid molecule can encode proteins derived from tumor associated antigens or antigens derived from viruses, bacteria, parasites, etc. By utilizing these second nucleic acid molecules, vaccines or drugs useful for treating cancer, viral infections, bacterial infections, parasitic infections, fungal infections, and other diseases, such as autoimmune diseases, can be produced.

2) Identifying New Vaccine Candidates to Elicit Cell-Mediated Immune Response

In another aspect of the invention, polypeptides delivered into the phagosomal compartment of mammalian cells may be processed by the cell to induce class II MHC-restricted cytotoxic T-lymphocyte (CTL) response, while those delivered into the cytoplasmic compartment may be processed to present antigens for a class I MHC-restricted CTL response. The ability to purify fusion proteins containing InvX or another peptide incorporating the 58 amino acid import region of Mce1A enables us to use them to deliver them into either compartment of the cells. To deliver them into the phagosomal compartment, one can impregnate biodegradable polymer microspheres with the fusion proteins. These matrix-bound proteins will preferentially enter phagosomes, and the polymer will undergo fragmentation inside the phagosomes to release the proteins: If the proteins are delivered without association with any polymer matrices, or are complexed to nanoparticles they will preferentially enter the cytoplasmic compartment of cells. This will enable the screening of a large number of such fusion polypeptides for candidates that may elicit the appropriate protective CTL response.

However, a polypeptide alone may not be sufficient to elicit a protective immune response. The advantage of this approach to identifying new effective vaccines compared to all other systems is the ability of InvX or another peptide incorporating the 58 amino acid import region of Mce1A to deliver any type of protein into cells. That is, if such a fusion protein can be expressed by a simple *E. coli* host, such a protein can be expressed by other hosts that will introduce post-translational modifications to the protein. By expressing invasive polypeptides by other host systems such as yeasts, insect cells, or mammalian cells, we may be able to introduce modifications such as glycosylation that may be important for eliciting protective immune response. Hence, unlike the products obtained from DNA delivery, we can introduce the polypeptides into mammalian cells that are modified before delivery. This is a clear advantage no other existing systems have.

3) Screening a Genome of a Pathogen for Immunodominant and/or Immunoprotective Peptide Sequences Previous methods of identifying new vaccine candidates involved examination of a single protein or polypeptide at a time. Such an approach takes a long time to determine if the polypeptide is protective or not, and does not offer a clear-cut opportunity to determine if the protection that is elicited is mediated by the CTL or humoral response, because the polypeptide may or may not enter cells. Using the fusion proteins of the invention, one can deliver such polypeptides into cells. Hence, the system is designed to maximize an opportunity to elicit a CTL response.

Furthermore, the fusion proteins of the invention provide an opportunity to create an expression library from the entire genome of a pathogen. That is, the entire coding repertoire of a pathogen can be expressed as fusion proteins and used to screen for the protective set of polypeptides, because all of the polypeptides can be made to enter cells.

For example, one can use the fusion proteins of the invention to develop a *Salmonella enteritidis* vaccine to be used to protect against bacteremia and ovarian infection in chickens. The entire *S. enteritidis* genome is cloned into fusion protein expression vectors as 1000-bp fragments, and all open reading frames thus cloned are expressed as fusion polypeptides. These polypeptides (>25,000) are divided into pools of about 2500 polypeptides and each pool is evaluated for its ability to protect mice from bacteremia after oral *S. enteritidis* challenge. The most protective pool is divided further into smaller pools and each pool is tested again for protection. This is repeated until a set of 5–10 polypeptides most protective against *S. enteritidis* infection is identified. The amino acid sequences of these polypeptides is examined to determine if they share any peptide sequences suggesting that they represent the immunodominant/immunoprotective epitopes.

4) Treatment of Cancer The fusion proteins of the present invention can be used to treat a variety of cancerous conditions. These include melanoma, ovarian cancer, breast cancer, prostate cancer, lung cancer, leukemia, or cancers of the other organs. These cancers are desirably treated by using the fusion protein of the present invention wherein the second protein is an anti-cancer protein or peptide. Exemplary, but limiting anti-cancer peptides or proteins include tumor suppressor proteins, such as p53, pRB, and FHIT (Fragile histidine triad).

5) Treatment of Pathogenic Diseases

Pathogenic diseases can also be treated with the fusion protein of the present invention. Such diseases may be caused by viruses, bacteria, parasites, and fungi. In these therapies, the second protein of the fusion protein is derived from these pathogens.

An effective amount of the fusion proteins wherein the second peptide is an anti-pathogenic peptide can be administered alone or in combination with a pharmaceutically-acceptable carrier to humans to achieve a particular therapeutic effect. Alternatively, it is possible to administer to subjects an antibody or binding portion thereof against the fusion proteins as a passive immunization. Such antibodies or binding portions thereof or probes are administered alone or in combination with a pharmaceutically-acceptable carrier.

Antibodies suitable for use in inducing passive immunity can be monoclonal or polyclonal. Such antibodies can be made by procedures well known in the art as outlined in U.S. Pat. No. 6,224,881.

Exemplary, but not limiting anti-pathogen peptides or proteins include granulysin, gramicidin, azurocidin, and membrane-active cyclic peptides.

6) Administration of Bioactive Fusion Proteins

The delivery of polypeptides into mammalian cells is not limited to identifying vaccine candidates. Peptides find use as antibiotics and anti-neoplastic agents. Such peptides must be delivered inside cells to work against tumor cells or intracellular pathogens. The fusion proteins of the invention can facilitate such intracellular delivery. There are peptides that affect expression of oncogenes and cell cycling, that if delivered into the proper compartment of cells, may affect cell replication, such that tumorgenesis may be controlled. The fusion of these peptides may be delivered orally, parenterally, intrathecally, or even by aerosols to target organs affected by neoplasm or infection.

The fusions polypeptides of the invention can also be used to deliver products to be absorbed by skin. This capability offers an unlimited application for cosmetic products, in addition to drugs used in cardiovascular, neurologic, and metabolic diseases. For instance, insulin in diabetes may be given with a skin patch instead of needles. The ability to deliver drugs via the skin offers possibilities and safety previously unenvisioned.

The fusion proteins of the present invention can be administered orally, parenterally, for example, subcutaneously, intravenously, intramuscularly, intraperitoneally, by intranasal instillation, or by application to mucous membranes, such as, that of the nose, throat, and bronchial tubes. They may be administered alone or with suitable pharmaceutical carriers, and can be in solid or liquid form such as, tablets, capsules, powders, solutions, suspensions, or emulsions.

A particular advantage of the fusion protein of the present invention is that it can be administered transdermally (e.g., with a patch) making it particularly useful in treating a variety of conditions. For example, it is useful in administering to diabetics their daily insulin dosage. Other conditions which may be treated transdermally with fusion proteins in accordance with the present invention include hypertension, angina, peripheral vascular disease, asthma, hypersensitivity, etc.

The solid unit dosage forms can be of the conventional type. The solid form can be a capsule, such as an ordinary gelatin type containing the fusion proteins of the present invention and a carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents such as, cornstarch, potato starch, or alginic acid, and a lubricant like stearic acid or magnesium stearate.

The fusion proteins of the present invention may also be administered in injectable dosages by solution or suspension of these materials in a physiologically acceptable diluent with a pharmaceutical carrier. Such carriers include sterile liquids such as water and oils, with or without the addition of a surfactant and other pharmaceutically acceptable adjuvants. Illustrative oils are those of petroleum, animal, vegetable, or synthetic origin, for example, olive oil, peanut oil, soybean oil, or mineral oil. In general, water, saline, aqueous dextrose and related sugar solution, and glycols such as, propylene glycol or polyethylene glycol, are preferred liquid carriers, particularly for injectable solutions.

For use as aerosols, the fusion proteins of the present invention may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

The invention will be better understood by reference to the following non-limiting examples.

EXAMPLES

EXAMPLE 1

Inv3 and Cell Adhesion

Inv3-β-gal constructs were prepared and expressed in *E. coli*. The Inv3-β-gal was purified and assayed for cell adhesion and import. While Inv3-β-gal adhered to HeLa cells, it was not imported into cells. *E. Coli* expressing the Inv3-β-gal fusion protein adhered to HeLa cells. While Inv3-β-gal fusion protein treated cells showed staining for β-gal activity over cells treated with β-gal alone, colloid gold particles coated in purified Inv3-β-gal failed to consistently detect intracellular gold particles above background level, suggesting that Inv3 fusion proteins are capable of mediating cell adhesion but that their cell import activity appears less than for Inv3 alone.

A. Construction of pInv3

The coding sequence of the whole protein Mce1A (67–1365) was amplified by PCR using H37Ra genomic DNA as template. The PCR product was cloned between Sph I and Kpn I sites of the vector pQE32 (Qiagen, Santa Clarita, Calif.) and the resulting construct was designated pMce1A. Two plasmids, pMce1a and pInv3, that contain partial sequences of mce1A gene were also constructed. pMce1a was constructed by amplifying 316 to 918 of mce1A by PCR and cloning into Bam HI site of pQE32. The pInv3 was constructed by cloning the sequence between nucleotide 388 and 453 of mce1A between Bam III and Sph I site of pQE30 downstream of a polyhistidine tag sequence. The polyhistidine tag enabled expression of a fusion protein with a hexa-histidine peptide sequence at the N-terminus, which facilitated ready purification of the protein using a nickel resin column.

Appropriate linkers were added to PCR primers to facilitate cloning for the constructs mentioned above. The construct for the Inv3 chimeric protein with β-galactosidase, pInvLZ, was made by inserting the Sal I fragment of pMC 1871 (Pharmacia, Uppsala, Sweden) into Sal I site of pInv3. The control plasmid, PQELZ, was constructed similarly in the vector pQE30. All recombinant plasmids were constructed and passaged in the E. coli strain M I 5[pREP4] (Qiagen, Santa Clarita, Calif.).

The pInv3 plasmid also has a polycloning site downstream of the inv3 sequence, followed by a termination codon. Hence, any polypeptide-coding DNA fragment can be cloned into the polycloning site and expressed as a fusion protein that will contain a histidine tag, followed by the Inv3 peptide sequence, followed by the heterologous polypeptide sequence. The presence of Inv3 at the N-terminus is what will permit the polypeptide (e.g., β-galactosidase) to enter mammalian cells.

B. Purification of rMce1A

E. coli M15[pREP4] (Qiagen, Santa Clarita, Calif.) was freshly transformed with pMce1A plasmid and cultured overnight in superbroth (Ausubel, 1994). The overnight culture was diluted in fresh medium and cultured at 371C with shaking until it reached mid-log phase, after which the culture was induced with 2 mM IPTG for 5 hours at 37° C. The induced culture was harvested, lysed in cracking buffer (Ausubel, 1994) and loaded onto 8% SDS-PAGE (Sambrook et al, 1989). After electrophoresis, the protein band corresponding to the rMce1A was excised from the gel and electroeluted. rMce1a was purified using Ni-NTA column (Qiagen, Santa Clarita, Calif.) following manufacturer's procedures under denaturing conditions.

Figure 2:
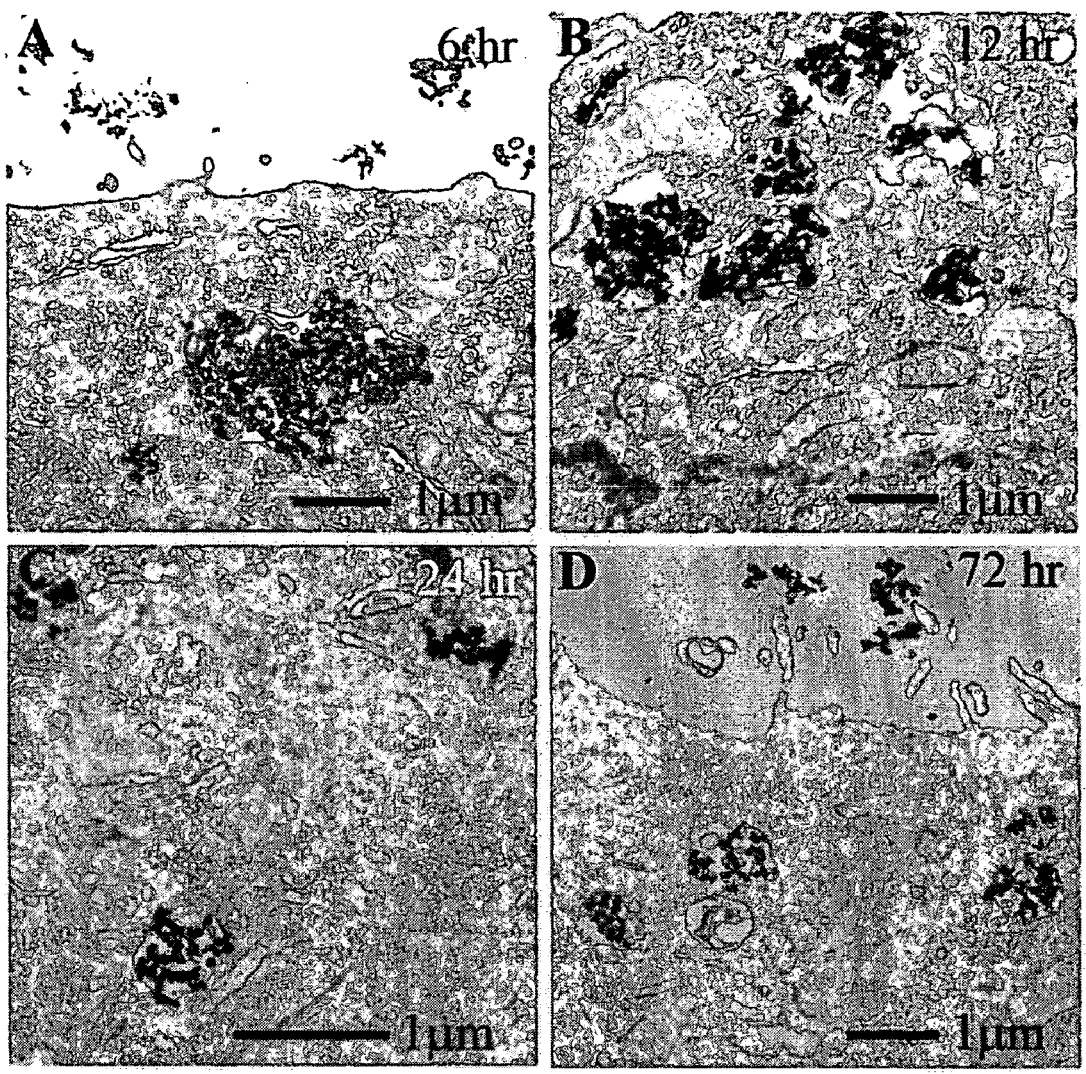
FIG. 2 shows that the peptide Inv3 efficiently mediates cellular import of colloidal gold particles by HeLa cells. HeLa cells were incubated with colloidal gold particles coated with Inv3 for 6 (A), 12 (B), 24 (C) and 72 hours (D). Scale bars are as labeled.

C. Expression of the Inv3-β-Galactosidase Fusion Protein pInv3 was used to express the enzyme β-galactosidase in E. coli M15. The expression and activity of E. coli expressing Inv3 β-galactosidase fusion protein was compared to those of the same E. coli host expressing β-galactosidase only. It was demonstrated that the former E. coli recombinant fusion protein associated abundantly with HeLa cells, while the latter fusion protein showed only background association (FIG. 2). Hence, the presence of the Inv3 sequence at the N-terminus of this β-galactosidase facilitates association of an E. coli host expressing the protein.

D. Purification of the Inv3-β-galactosidase Fusion Protein

Inv3-β-galactosidase and β-galactosidase were purified using a nickel column (Qiagen, Santa Clarita, Calif.) following manufacturer's procedures under native conditions. HeLa cells were incubated with the purified proteins. At 200 μg/ml concentration of each purification, 100% of the cells in the monolayer incubated with the Inv3-β-galactosidase fusion protein turned blue after staining (indicating enzyme activity), while only a few of the cells showed blue staining among those incubated with β-galactosidase. Hence, the Inv3-β-galactosidase fusion protein adhered to the cells, but import into HeLa cells was not observed.

E. Cell Import Assay and Electronmicroscopy

Proteins used for electronmicroscopy analysis were dialyzed extensively with water after purification, and subsequently adjusted to a concentration of 0.5 mg/ml. HeLa cells were used in all assays and maintained in Dulbecco's Modified Eagle Medium (DMEM) (Gibco BRL, Gaithersburg, Md.) supplemented with 10% fetal bovine serum (FBS) (Gibco BRI., Gaithersburg, Md.). Ten nm colloidal gold particles in 8 ml suspension (Sigma, St. Louis, Mo.) were pelleted, and 0.5 ml of the protein solution to be tested were added to the pellet and the pellet was resuspended in the protein solution. the mixture was incubated at room temperature for 30 minutes. After incubation, 1 ml of stabilizing solution (0.15M NaCl 0.05M Tris-HCl pH9, and 0.5 mg/ml Carbowax 20-M) was added and the colloidal gold particles were spun down, washed once with sterile phosphate buffed saline (PBS) (Sambrook et al., 1989) and resuspended in 25 μl of PBS. The coated colloidal gold particles were then added to near confluent HeLa cells in a 25 cm$^2$ tissue culture flask and the cells were incubated at 37° C. in 5% $CO_2$ for desired length of time. After incubation, cells were washed five times with PBS and fixed in 3% glutaraldehyde in PBS overnight at 4° C. The fixed cells were scraped off flasks and embedded for electronmicroscopy analysis.

For assays testing the effects of cytoskeleton inhibitors, HeLa cells were incubated with 0.1 μg/ml of cytochalasin D or 1 μg/ml nocodazole for 1 hour at 37° C. or 4° C. respectively. Cells were then added with colloidal gold particles coated in rMce1a and incubated at 37° C. overnight. The samples were then washed 5 times in PBS, fixed in 3% glutaraldehyde overnight and processed for electron microscopic analysis.

The samples for electronmicroscopy analysis were processed as described (Dernburg et al, 1998). The thin sections (60 nm) were made and post stained in uranyl acetate and lead citrate. All samples were observed under JEOL JEM I OOCX transmission electronmicroscope.

Ten nm colloidal gold nanoparticles were used as vehicles to study the kinetics of Mce1 A-mediated import by non-phagocytic mammalian cells and their trafficking inside these cells. Recombinant Mce1A proteins were expressed in and purified from E. coli. The rMce1A is the full-length 45-KD protein, and rMce1a (SEQ ID NO:2) is a 27-KD truncated form of Mce1A that lacks 105 amino acids at the N-terminus and 147 amino acids at the C-terminus. After 18 hours of incubation with HeLa cells, large quantities of both rMce1A and rMce1a coated colloidal gold particles were detected inside the cells by transmission electronmicroscopy (TEM). The rMce1A and rMce1a showed identical characteristics in the cell import assays although rMce1a seems to have higher activity, and they were used interchangeably in the subsequently assays. Most of the internalized colloidal gold particles were observed inside vacuoles. The morphology of cell membrane around the Mce1A coated gold particles suggested that the particles initiated their cell entry by inducing invagination of the plasma membrane. Subsequently the invagination deepened and the cell membrane fused distally to completely surround the gold. The vacuoles closest to the cell surface (presumably newly formed) were usually more spacious, while those located more centrally were tightly apposed to the clusters of gold particles. In most cases, the cells contained multiple vacuoles with a varying number of Mce1A coated gold particles and no visible damage to the cells was observed.

Although most of the internalized Mce1A coated gold particles were enclosed in membrane bound vacuoles, a small number of them was observed exposed to the cytosol. Some Mce1A coated gold particles were observed to enter cells through gap-like spaces in the plasma membrane. The morphology of the gaps appears similar to that induced by reovirus during endocytosis by host cells (Wolf et al., 1981). It is not known if the Mce1A coated gold particles themselves induced the gaps in the plasma membrane or that they simply took advantage of the naturally occurring gaps in the membrane to enter. However, control gold particles coated with bovine serum albumin (BSA) were not found to enter cells through gaps in the membrane, suggesting Mce1A is playing a role in this entry process. Other cytosol-exposed gold particles were clustered together. The clustered morphology of these particles suggests that they might have initially been enclosed in vacuoles and subsequently the vacuolar membrane disintegrated.

Gold particles coated with BSA were used as negative control in all experiments. The gold particles were rarely observed inside cells. However, tiny patches of BSA coated particles were occasionally observed inside cells (2–4% of cells) and they were surrounded by vacuoles. In comparison, Mce1A-coated gold particles were consistently detected in >30% of the monolayer of cells and with a much larger number of gold particles per cell.

F. Adherence Assays

HeLa cells were plated at $5 \times 10^4$ cells/well in 24-well tissue culture plates the day before the assay. For adherence assays using *E. coli* hosts, M 15 [pREP41] was freshly transformed with plasmid expressing the recombinant protein to be assayed and cultured overnight. On the day of assay, the overnight bacterial culture was diluted in fresh medium and induced with 2 mM IPTG for 2 hours at 37° C. The induced culture was washed once with PBS, and resuspended in equal volume of PBS. Before adding *E. coli* to the cells, cells were changed with fresh medium (DMEM supplemented with 10% FBS) containing 1% manose and incubated at 37° C. for 30 minutes. Five or 10 microliters of bacteria suspension was added to each well and samples were incubated at 37° C. for 5 hours. After incubation, cells were washed five times with PBS, fixed in 2% paraformaldehyde for 20 minutes at 4° C. and washed twice with 1313S to remove the fixative. The samples incubated with *E. coli* expressing β-gal or Inv3-β-gal were stained in PBS containing 0.27 mg/ml spermidine, 2 mM $MgCl_2$, 0.02% NP40, 0.01% sodium deoxycholate, 5 mM potassium ferrocyanide, 4.5 mM potassium ferricyanide and 5 mg/ml X-gal for 2 hours at 37° C. and post fixed in 2% paraformaldehyde at 4° C. for 20 minutes. The samples were then washed twice briefly with PBS, mounted in Fluoromount and observed under a light microscope.

The adhesion assays with purified recombinant proteins were carried out similarly as those using *E. coli* expressing the recombinant proteins, except that purified proteins were added to the HeLa cells.

G. Time Course of rMce1A Mediated Cellular Import of Colloidal Gold Particles

The kinetics of cell import of HeLa cells by full length Mce1A coated gold particles and their trafficking inside the cells were analyzed. The coated gold particles were incubated with HeLa cells from 6 to 72 hours, and samples were processed for analysis by TEM. At 6 hours, most of the gold particles could be seen in the process of invading HeLa cells. Pronounced filopodia formation could be observed adjacent to the gold particles, and a cluster of gold particles were seen to be completely internalized, presumably from the fusion of plasma membrane that surrounded the particles. At 12 and 24 hours, an increased number of gold particles inside cells with multiple gold-containing vacuoles were observed. More tightly apposed gold particle-containing vacuoles were observed during this time than at 6 hours, possibly reflecting the maturation of these vacuoles. The cellular import process of full length Mce1A-coated colloidal gold particles by HeLa cells appeared to be continuous. At any time point, particles could be seen at the initial stages of cell entry. Small number of gold particles could also be seen in the cytosol at all time points examined.

The cells in the cell import assays showed normal morphology even after ingesting a large number of colloidal gold particles over a 72-hour incubation period. No obvious cell death was observed in any assay of any duration of incubation as determined by trypan blue dye exclusion.

H. Cytoskeleton Inhibitors Block the Cellular Import of Mce1A-Coated Colloidal Gold Particles To study if cytoskeletal rearrangement is involved in the cellular import of Mce1A-coated particles as suggested by the observed morphological changes of cells, HeLa cell import assays of rMcela coated gold particles were carried out in the presence of nocodazole or cytochalasin D, which inhibits microtubule and microfilament rearrangement, respectively. In the presence of nocodazole, no gold particle was observed inside the cells. In the presence of cytochalasin D, the amount of gold particles observed inside the cells was greatly reduced, although not completely abolished. Tiny patches of gold particles could be observed in some of the cells. In the absence of inhibitors, cells were observed to contain much larger quantities of gold particles. This observation suggests that both microtubules and microfilaments are involved in the cellular import of the Mce1A coated colloidal gold particles. This is consistent with the plasma membrane perturbation elicited by coated particles as observed by TEM.

I. Cell Association of Inv3-β-Gal Fusion Protein

Figure 3:
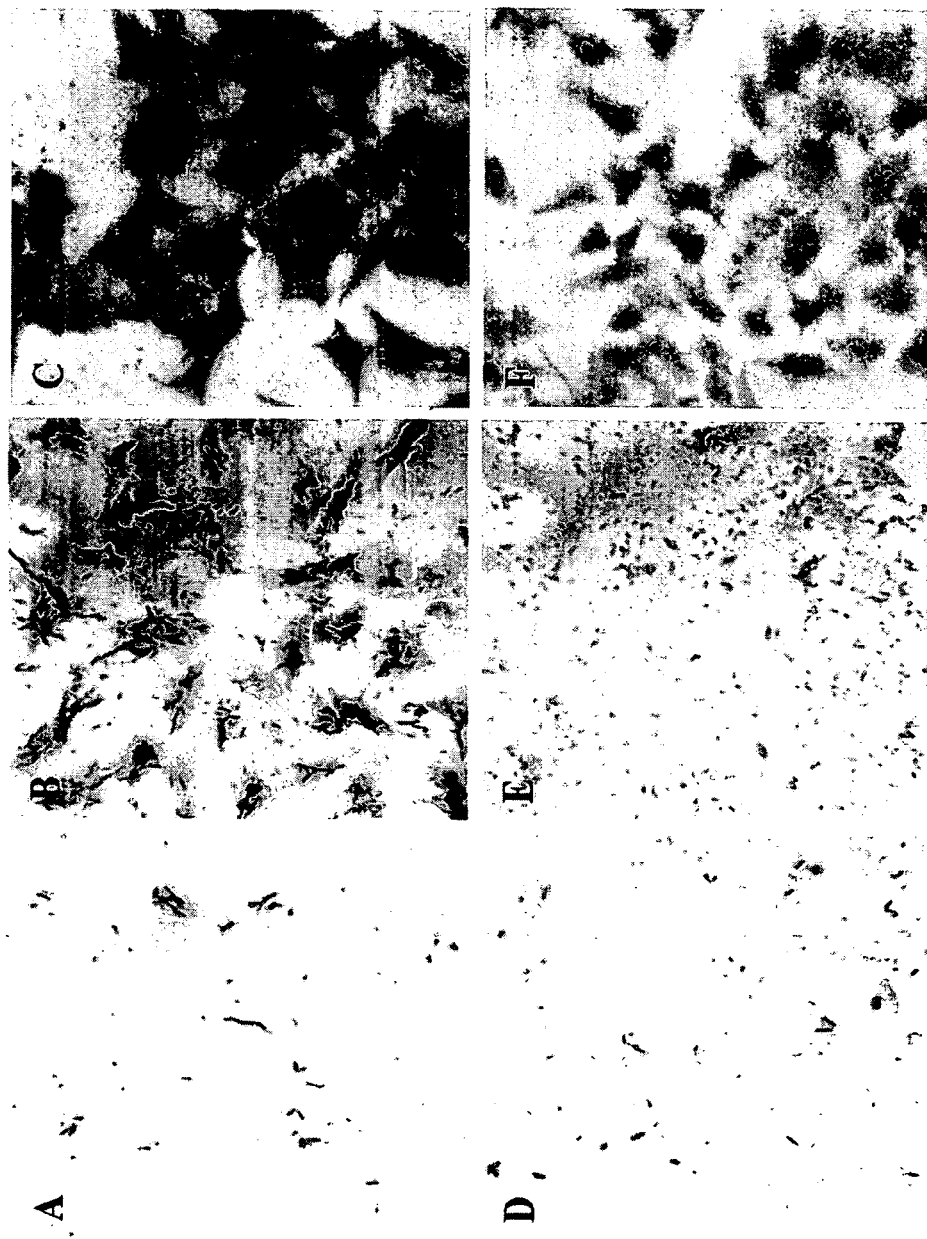
FIG. 3 shows that Inv3-β-gal chimeric protein mediates adhesion to HeLa cells. HeLa cells were incubated with E. coli transformed with pQELZ and cultured under IPTG induction (A) or no induction (D), or pInv3LZ and cultured under IFTG induction (B) or no induction (E). HeLa cells were also incubated with purified protein Inv3–13-gal (C) or-β-gal (F).

Inv3 fusion proteins are less capable than Inv3 alone in facilitating import of non-covalently associated colloid gold particles. The plasmid pinvLZ expressed a chimeric protein of Inv3 and β-gal (Inv3-β-gal) when induced by isopropyl-β-D-thiogalactoside (IPTG). Another expression plasmid, pQELZ, which expresses β-gal under IPTG induction, was used as the control. *E. coli* transformants of pinv3LZ grown under IPTG induction associated with HeLa cells efficiently, while those grown without IPTG induction showed little cell association (FIGS. 3B and 3E). The pQELZ transformed *E. coli* did not associate with cells regardless of IPTG induction (FIGS. 3A and 3D). To determine if Inv3 peptide alone was responsible for the cell association property of the chimeric proteins, we purified Inv3-β-gal from *E. coli* and used it to perform a cell association assay. HeLa cells incubated with Inv3-β-gal showed prominent staining for β-gal activity compared to those incubated with β-gal alone (FIGS. 3C and 3F). TEM analysis of cell import of HeLa cells by colloidal gold particles coated in purified Inv3-β-gal failed to consistently detect intracellular gold particles above the background level. In all samples 2 or 3 cells contained tiny patches of gold particles in a total of 50 cells observed. These results suggest that Inv3 is capable of mediating cell association of covalently linked 13-gal, but that its cell import activity appears to be less than that of the Inv3 peptide alone.

Figure 4:
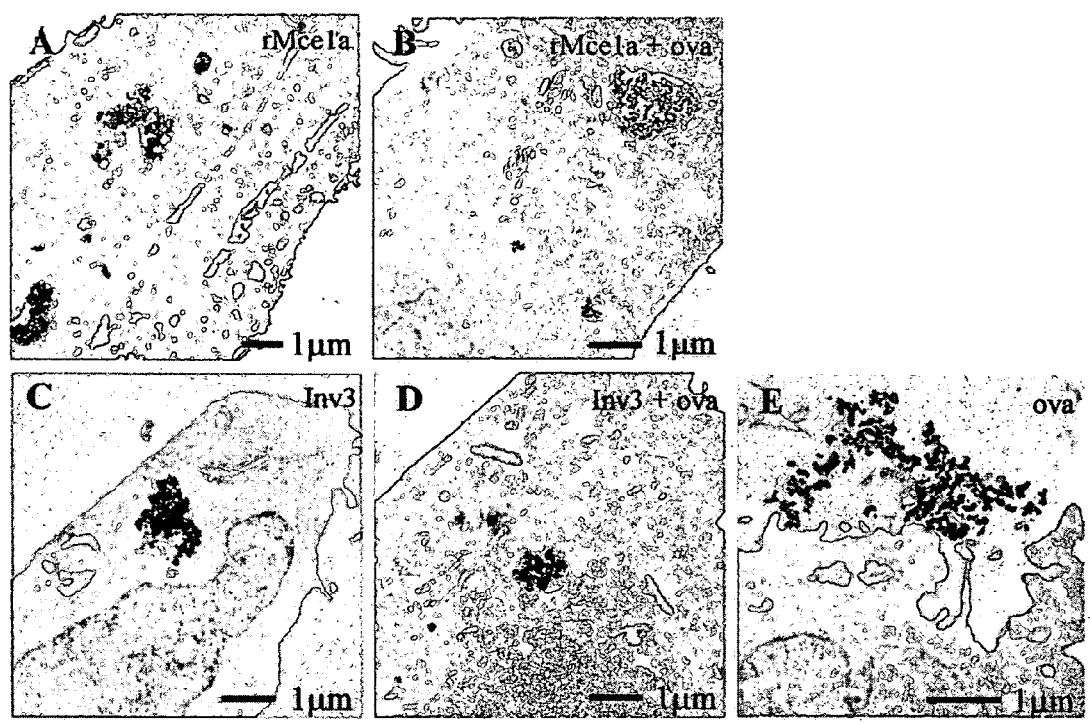
FIG. 4 shows that rMce1a and Inv3 mediate cellular import of heterologous colloidal gold particles coated with mixtures of rMce1a or Inv3 with chicken ovalbumin. (A), rMce1a; (B), rMce1a and ovalbumin; (C), Inv3; (D), Inv3 and ovalbumin and (E) ovalbumin only ova, ovalbumin. Scale bars are as labeled.

J. Delivery of Unfused Inv3 Mediated Import of Non-Covalently Associated, Heterologous Proteins into Cells Non-fusion Inv3 or rMcela mediate the import of heterologous, non-covalently attached proteins when a mixture of the protein and Inv3 or rMcela as non-fusion proteins is used to coat the colloidal gold particles. Chicken ovalbumin was used as a test protein in this assay. Cell import assays were carried out with colloidal gold particles coated in ovalbumin, or a mixture of ovalbumin and Inv3 or rMcela. TEM analysis indicated that colloidal gold particles coated with ovalbumin alone were not taken up by HeLa cells, while those coated with the protein mixtures were taken up by HeLa cells as efficiently as those coated in Inv3 or rMcela (FIG. 4). As noted above, however, Inv3 fusion proteins mediated cell entry of heterologous, non-covalently associated colloid gold particles less efficiently than Inv3.

Example 2

Cell Adhesion and Import by InvX Fusion Proteins

Unlike Inv3-β-gal fusion proteins, a 72 amino acid InvX (SEQ ID NO:6) fusion protein mediated efficient cell adhesion and import of E. coli and colloid gold particles. The InvX-AIDA expressing E. coli showed a greater association with HeLa cells than in a control strain. Unlike the Inv3 fusion protein, the InvX fusion protein facilitated both cellular adhesion and import efficiently. Further, the InvX fusion protein was sufficient for cellular import both colloid gold particles and E. coli, and facilitated superior cellular import of colloid gold particles to the Inv3-β-gal fusion protein.

A. Bacterial Strains and Cell Line Selection

E. coli strain UT4400, an ompT-negative derivative of UT2300, was the host strain used in all experiments. The references cited in this Example are listed numerically at the end of the Example before the claims. E. coli was routinely grown in Luria-Bertani media supplemented with 100 μg/ml ampicillin or 50 μg/ml kanamycin to maintain plasmids. The human epithelial cell line, HeLa (ATCC CCL-2), was maintained in Dulbecco's Modified Eagle Medium (DMEM) supplemented with 10 mM sodium pyruvate, 10% fetal bovine serum and 10 μg/ml penicillin/streptomycin.

B. Construction of Vectors

InvX is presented on the surface of E. coli by the AIDA autotransporter translocator. The plasmid pMK90 expresses a recombinant AIDA autotransporter that has been modified by removing its passenger domain to permit cloning of heterologous polypeptides. A 72 amino acid region of Mce1A (positions 106–177) termed InvX (SEQ ID NO:6), that contains the 58 amino acid putative active domain with short flanking regions (18), was cloned into the AIDA vector resulting in the construct pMK100.

The plasmid pMK90 is an ampicillin resistant pBR322-derivative that expresses a recombinant AIDA protein under the control of its own promoter (19). The AIDA coding sequence has been altered to remove the native passenger; it includes a 49 amino acid signal peptide, a 78 amino acid linker region incorporating a multiple cloning site, and the entire 440 amino acid β-barrel core. A 240 bp DNA fragment encoding InvX (M. tuberculosis H37Rv genome position 198847–199063) was amplified by PCR from a plasmid containing mce1A and cloned into pMK90 generating pMK100. E. coli harboring pMK90, which expresses the AIDA autotransporter translocator with no passenger, and pMK100, which expresses the InvX-AIDA fusion, were used in the following assays. Plasmid pMS2kan expresses a kanamycin resistance marker.

C. Cell Import and Adhesion Assays

Gentamicin protection assays were performed according to Elsinghorst (20). HeLa cells were seeded at $1 \times 10^5$ cells per well onto cover slips or directly into 24-well plates and cultured for 24 h until confluent. Cell culture media was modified to contain 1% mannose and no antibiotics. Recombinant E. coli were added to the monolayer at a multiplicity of infection (MOI) of 10:1 and incubated at 37° C. for 3 h. To determine associated (adherent and intracellular) bacteria, we washed the monolayer three times with phosphate buffered saline (PBS) and subsequently lysed the cells in 0.1% Triton-X100 (Bio-Rad Laboratories, Hercules, Calif.). Alternatively, washing was followed by incubation with medium containing 100 μg/ml gentamicin (Sigma Chemical Co., St. Louis, Mo.) for 1 h to kill extracellular bacteria and permit enumeration of intracellular bacteria. The monolayer was again washed three times with PBS and lysed. Serial dilutions of released bacteria were plated for counting. Associated and invaded bacteria are presented as a percentage of the inoculum; results shown are the mean values for a representative experiment performed in triplicate ±S.D.

In some experiments HeLa cells were pretreated with various concentrations of inhibitory agents; inhibitors were kept in the medium throughout the experiment. Cytochalasin D (Sigma Chemical Co.) was added at 0.01–1 μg/ml and the cells incubated at 37° C. for 30 min prior to infection. Nocodazole (Sigma Chemical Co.) was used at 0.5–10 μg/ml with preincubation for 1 h at 4° C. followed by warming to 37° C. for 30 min. Clostridium difficile Toxin B (Sigma Chemical Co.) was added at 10 ng/ml and incubation continued for 20 h at 37° C. before the addition of bacteria. The effect of inhibitors on HeLa cell viability was assessed using the trypan blue exclusion assay (2) and the effect on the growth of the recombinant E. coli strains in supplemented DMEM was determined.

After infection, HeLa cells seeded onto cover slips were fixed in ice-cold methanol at 4° C. for 10 min and stained with SureStain Wright-Giemsa (Fisher Scientific, Pittsburgh, Pa.) at room temperature for 10 min. Cover slips were washed three times in water and mounted onto microscope slides with CytoSeal (Stephens Scientific, Riverdale, N.J.). Slides were viewed by a Nikon Optiphot-2 microscope and photographed with a Sony DKC-5000 digital camera.

Figure 5:
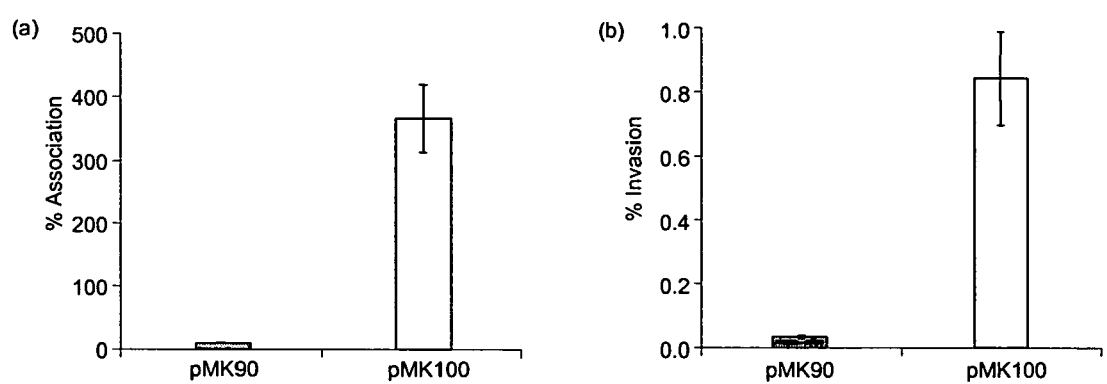
FIG. 5 shows InvX-mediated cellular adhesion to and import into HeLa cells. HeLa cells were infected with E. coli harboring the InvX-expressing plasmid pMK100 or the control plasmid pMK90 at an MOI of 10:1 for 3 h. Bars represent the mean number of associated (a) or intracellular (b) bacteria as a percentage of the inoculum in a representative experiment performed in triplicate. Standard deviations are marked by error bars.
Figure 6:
FIG. 6 shows InvX-mediated adhesion to HeLa cells. HeLa cells were infected with the E. coli(pMK90) control strain (a) or E. coli(pMK100) expressing InvX (b) at an MOI of 10:1. After 3 h the monolayer was washed thoroughly and stained with Giemsa to visualize bacterial attachment. Magnification×400.
Figure 6:

InvX can mediate adhesion to HeLa cells and is sufficient for internalization. InvX-expressing E. coli showed 40-fold greater association with HeLa cells than the control strain (FIG. 5). The recombinant E. coli had a doubling time of approximately 1 h in tissue culture medium; hence, the level of association was calculated at almost 400% of the inoculum. Adherence was also assessed microscopically by Giemsa staining. E. coli (pMK100) showed extensive association with HeLa cells forming dense lacy networks on the monolayer, whereas the control strain showed little adherence (FIG. 6).

Figure 7:
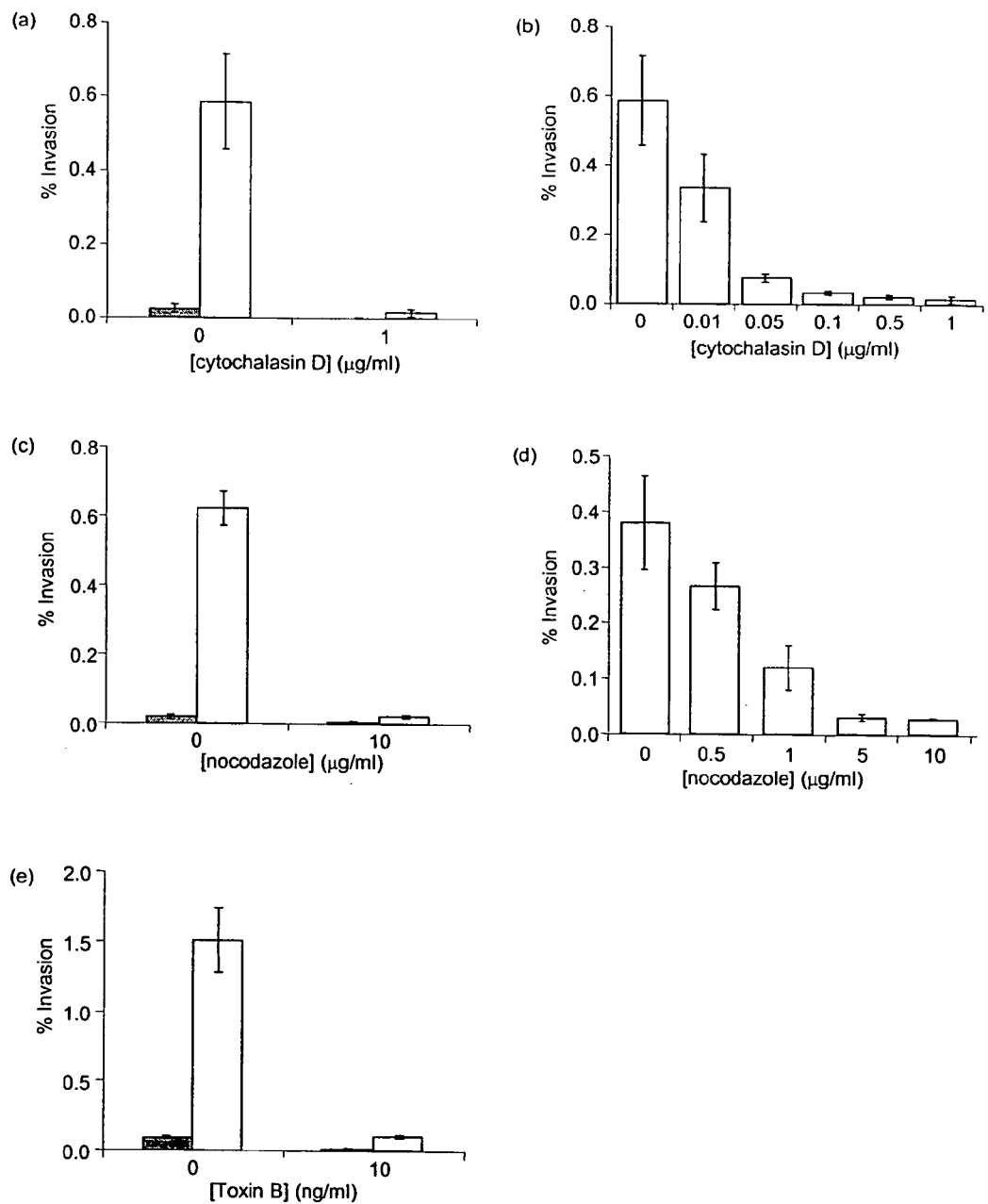
FIG. 7 shows the effect of cytoskeletal inhibitors on InvX-mediated cellular import. Gentamicin protection assays were used to determine the affects of cytochalasin D (a, b), nocodazole (c, d) and Toxin B (e) on the level of import of E. coli(pMK90) (shaded bars) and E. coli (pMK100) (white bars) into HeLa cells. Bars represent the mean number of internalized bacilli from a representative experiment performed in triplicate. Standard deviations are marked by error bars.

The ability of InvX to mediate import of the host E. coli using gentamicin protection assays was assessed (20). Since gentamicin is unable to penetrate mammalian cell membranes, gentamicin-protected bacteria are located intracellularly. E. coli(pMK100) showed 25-fold higher cell import levels than the control with 0.8% of the inoculum protected (FIG. 5b). In order to confirm that the gentamicin-protected bacteria truly resided intracellularly, we additionally examined infected cells by electron microscopy (FIG. 7). After 3 h incubation, E. coli(pMK100) showed extensive adherence to the HeLa cell surface and appeared to elicit filopodia-like membrane protrusions. Intracellular bacteria were seen in membrane-bound compartments, definitively demonstrating that they had been internalized. E. coli(pMK90) were rarely seen associated with HeLa cells and were never seen inside cells.

D. Electron Microscopy

Infected cells were prepared for examination by transmission electron microscopy as previously described (18). Briefly, cells were fixed in 2% glutaraldehyde and stained with osmium tetroxide solution before dehydration through graded ethanol solutions. Cells were embedded in Spur's low viscosity embedding media and ultrathin sections were stained with uranyl acetate and lead citrate. Samples were examined with a JEOL model 100CX-II transmission electron microscope.

E. Immunofluorescence Microscopy

E. coli were fixed onto microscope slides with 0.4% paraformaldehyde for 10 min at room temperature and nonspecific binding was blocked by incubation in 1% w/v bovine serum albumin for 30 min. Slides were incubated for 1 h with a 1:40 dilution of a mouse antibody raised against Mce1A (HI5), washed and incubated with a 1:100 dilution of FITC-labeled anti-mouse antibody (Sigma Chemical Co.) for 1 h. After extensive washing, the cover slips were mounted with SlowFade Light antifade reagent (Molecular Probes, Eugene, Or. Slides were viewed on a Nikon Eclipse TE300 inverted microscope with an epi-fluorescence attachment and photomicrography was performed with Nikon U-III equipment.

F. InvX is Presented on the Surface of *E. coli* by the AIDA Autotransporter Translocator The plasmid pMK100 was used to express a 72 amino acid region of Mce1A (positions 106–177), termed InvX, that contains the 58 amino acid putative active domain with short flanking regions in the AIDA autotransporter vector pMK90. An ompT-negative E. coli strain, UT4400, was used to express AIDA fusions, as OmpT is known to sometimes cleave surface-exposed passengers. Immunoblotting, using polyclonal antibodies raised against the core AIDA translocator or Mce1A, indicated that the expected fusion protein was expressed in E. coli UT4400 (pMK100) (data not shown). Surface expression of InvX was ascertained by loss of immunoreactivity with the anti-Mce1A antibody after trypsin digestion of whole cells (data not shown) and verified by indirect immunofluorescence of whole cells. The stable expression of InvX on the surface of *E. coli* by the AIDA autotransporter translocator enabled the detailed study of its interaction with HeLa cells using standard cell import assays.

G. Disruption of the Actin Cytoskeleton Inhibits Cell Import

To determine whether actin microfilaments were required for InvX-mediated cell import, HeLa cells were pretreated with cytochalasin D, which specifically inhibits actin polymerization. Gentamicin protection assays showed that treatment of cells with 1 g/ml cytochalasin D reduced import of *E. coli* (pMK100) to control levels and that inhibition of cell import was dose dependent (FIG. 7). HeLa cell viability and bacterial viability were not affected. Bacterial adhesion was also not affected by cytochalasin D treatment indicating that the role of actin microfilaments was in bacterial uptake.

H. Inhibition of Rho-Family GTPases Prevents Cell Import

To determine whether Rho, Rac or Cdc42, which are key regulators of the actin reorganization, were involved in InvX-mediated cell import, the HeLa cell monolayer was pre-treated with 10 ng/ml *C. difficile* Toxin B. Toxin B inactivates Rho family GTPases by monoglucosylation with a dominant negative effect. Toxin B treatment resulted in rounding-up of the HeLa cells but did not affect their viability. This pretreatment completely inhibited *E. coli* (pMK100) entry (FIG. 7e), but did not affect bacterial adhesion or viability.

I. Microtubule Disruption Inhibits Cell Import

To determine whether InvX-mediated cell import was also microtubule-dependent, the effect of pretreating HeLa cells with nocodazole was examined. Nocodazole specifically depolymerizes microtubules. Pretreatment with 10 µg/ml resulted in rounding of the cells without affecting viability. Nocodazole treatment clearly inhibited the uptake of *E. coli* (pMK100) reducing it to the level of the control, *E. coli* (pMK90) (FIG. 7c). Inhibition of cell import was dose dependent (FIG. 7d), but bacterial viability and association were not affected. Hence, *E. coli* expressing InvX require an intact microtubule network for entry but not for adhesion to HeLa cells.

J. Cell Import Does Not Affect Import of 'Bystander' Bacteria

Figure 8:
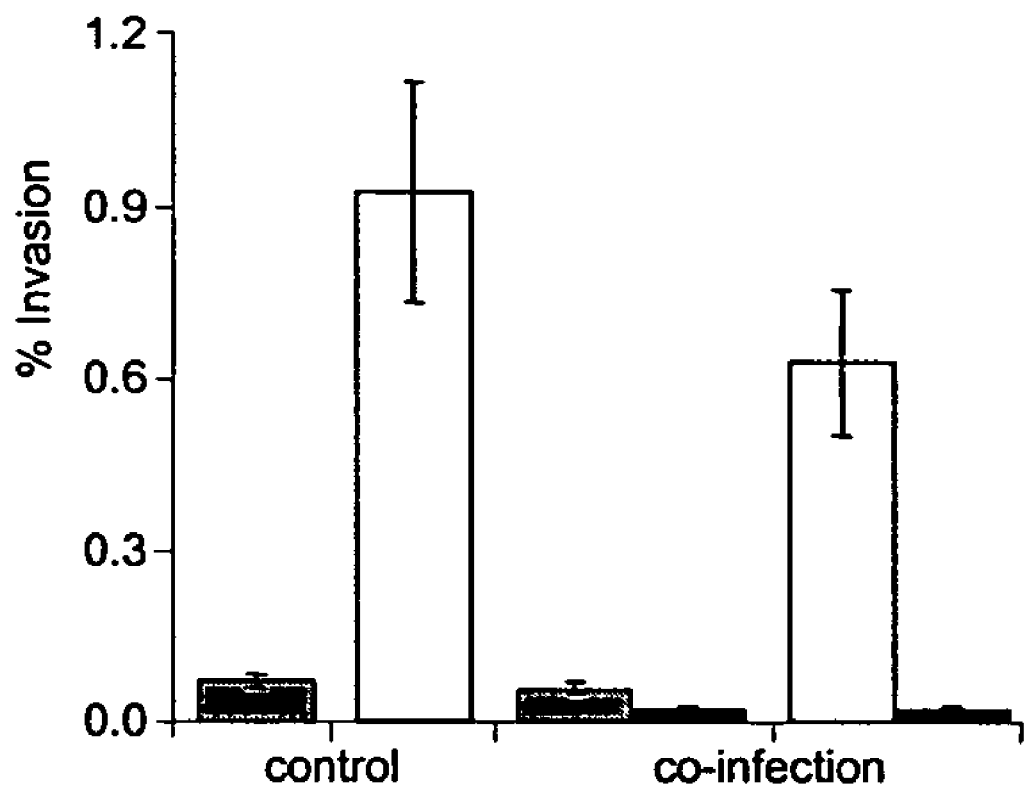
FIG. 8 shows the effect of InvX-mediated import on 'bystander' bacteria. Control HeLa cells were infected with either *E. coli*(pMK90) (shaded bars) or the InvX-expressing *E. coli* (pMK100) (white bars). In addition, HeLa cells were co-infected with the non-invasive bystander *E. coli* (pMS2) (black bars), in the presence of either *E. coli*(pMK90) or *E. coli* (pMK100). The number of internalized bacilli was determined in triplicate, using a gentamicin protection assay, and the mean result expressed as a percentage of the inoculum. Error bars indicate standard deviations.

We wished to determine whether internalization of InvX-expressing *E. coli* resulted in nonspecific import of proximal bacilli. Thus, HeLa cells were simultaneously infected with either *E. coli*(pMK100) or *E. coli*(pMK90), which carry an ampicillin resistance marker, and a second non-invasive recombinant *E. coli* strain expressing kanamycin resistance. Recovered intracellular bacteria were plated on ampicillin and kanamycin to determine whether nonspecific import occurred. No significant import of the non-invasive kanamycin-resistant strain was observed when co-infected with either *E. coli* (pMK100) or *E. coli* (pMK90) (FIG. 8).

Although the invention has been described in detail for the purpose of illustration, it is understood that such detail is solely for that purpose, and variations can be made therein by those skilled in the art without departing from the spirit and scope of the invention which is defined by the following claims.

THE FOLLOWING REFERENCES CITED HEREIN ARE HEREBY INCORPORATED BY REFERENCE IN THEIR ENTIRETY

1. Arruda, S., Bomfim, G., Knights R, Huima-Byron, T., and Riley. L. W. (1993) Cloning of an *M. tuberculosis* DNA fragment associated with entry and survival inside cells. Science 261:1454–1457.
2. Bliska, J. B., Galan, I. E., and Falkow, S. (1993) Signal transduction in the mammalian cell during bacterial attachment and entry. Cell. 73:903–920.
3. Cole, S. T., Brosch, R., Parkhill, J., Garnier, T., Churcher, C., Harris, D., Gordon, S. V. et al. (1998). Deciphering the biology of *Mycobacterium tuberculosis* from the complete genome sequence. Nature 393:537–544.
4. Fleiss, J. L. Statistical methods for rates and proportions. 2$^{nd}$ Ed. New York: John Wiley & sons. 1981.
5. Galan, J. E. (1996) Molecular genetic bases of *Salmonella* entry into host cells. Mol Microbiol. 20:263–71.
6. Hakansson, S., Galyov, E. E., Rosqvist, R., and Wolf-Watz, H. (1996) The *Yersinia* YpkA Ser/Thr kinase is translocated and subsequently targeted to the inner surface of the HeLa cells plasma membrane. Mol Microbiol. 20:593–603.
7. Hirsch, C. S., Elmer, J. J., Russell, D. G., and Rich, E. A. (1994) Complement receptor-mediated import and tumor necrosis factor-alpha-mediated growth inhibition of *Mycobacterium tuberculosis* by human alveolar macrophages. J. Immunol. 152:743–53.
8. McDonough, K. A. and Kress, Y. (1995) Cytotoxicity for lung epithelial cells is a virulence-associated phenotype of *Mycobacterium tuberculosis*. Infect. Immun. 63:4802–11.
9. Menard, R., Dehio, C., and Sansonetti, P. J. (1996). Bacterial entry into epithelial cells: the paradigm of *Shigella*. Trends in Microbiol. 4:220–226.
10. Morissey, J. H. (1981) Silver stain for proteins in polyacrylamide gels: a modified procedure with enhanced uniform sensitivity. Anal. Biochem. 117:307–310.
11. Persson, C., Nordfelth, R., Homstrom, A., Hakansson, S., Rosqvist, R., and Wolf-Watz, H. (1995) Cell-surfacebound *Yersinia* translocate the protein tyrosine phosphatase YopH by a polarized mechanism into the target cell. Mol. Microbiol. 18:135–50.
12. Rosqvist, R., Magnusson, K., and Wolf-Watz, H. (1994) Target cell contact triggers expression and polarized transfer of *Yersinia* YopE cytotoxin into mammalian cells. EMBO J. 13:964–972.
13. Schlesinger, L. S. (1993) Macrophage phagocytosis of virulent but not attenuated strains of *Mycobacterium tuberculosis* is mediated by mannose receptors in addition to complement receptors. J. Immunol. 150:2920–30.
14. Schlesinger, L. S., Bellinger-Kawahara, C. G., Payne, N. R., and Horwitz, M. A. (1990) Phagocytosis of *Mycobacterium tuberculosis* is mediated by human monocyte complement receptors and complement component C3. J. Immunol. 144:2771–80.
15. Shepard, C. C. (1957). Growth characteristics of tubercule bacilli and certain other mycobacteria in HeLa cells. J. Exp. Med. 105:39–55.
16. Shepard, C. C. (1958) A comparison of the growth of selected mycobacteria in HeLa, monkey kidney, and human amnion cells in tissue culture. J. Exp. Med. 107:237–45.
17. Tekaia F., Gordon, S. V., Garnier, T., Brosch, R., Barrell, G. G., and Cole, S. T. (1999) Analysis of the proteome of *Mycobacterium tuberculosis* in silico. Tubercle and Lung Dis. 79:329–342.
18. Chitale, S., Ehrt, S., Kawamura, I., Fujimura, T., Shimono, N., Anand, N., Lu, S., Cohen-Gould, L., and Riley, L. W. (2001), Recombinant *Mycobacterium tuberculosis* protein associated with mammalian cell entry, Cell. Microbiol., 3:247–254.
19. Benz, I., and Schmidt, M. A., (1992), Cloning and expression of an adhesin (AIDA-I) involved in diffuse adherence of enteropathogenic *Escherichia coli* Infect Immun. 57:1506–1511.
20. Elsinghorst, E. A. (1994), Measurement of invasion by gentimycin resistance, Methods Enzymol. 236: 405–420.

What is claimed:

1. A nucleic acid construct comprising:
   a first nucleic acid molecule encoding a first peptide comprising the amino acid sequence selected from the group consisting of SEQ ID NO:6, SEQ ID NO:8, and SEQ ID NO:10, and
   a second nucleic acid molecule encoding a second peptide, said second nucleic acid molecule being operatively coupled to said first nucleic acid molecule, wherein expression of the nucleic acid construct produces a fusion protein comprising said first peptide coupled to said second peptide.

2. The nucleic acid construct according to claim 1, wherein said first peptide comprises the amino acid sequence of SEQ ID NO:6.

3. The nucleic acid construct according to claim 1, wherein said first nucleic acid comprises a nucleotide sequence selected from the group consisting of SEQ ID NO: 5, SEQ ID NO: 7, and SEQ ID NO: 9.

4. The nucleic acid construct according to claim 3, wherein said nucleic acid comprises the nucleotide sequence of SEQ ID NO: 5.

5. The nucleic acid construct according to claim 1, further comprising a nucleic acid sequence encoding a linker peptide positioned between said first and second nucleic acid molecules.

6. The nucleic acid according to claim 1, wherein said second nucleic acid encodes a therapeutic peptide.

7. The nucleic acid according to claim 1, wherein said second nucleic acid encodes a diagnostic peptide.

8. An expression system transformed with the nucleic acid construct according to claim 1.

9. An expression system according to claim 8, wherein said expression system is selected from the group consisting of bacterial, yeast, insect, fish and mammalian cell expression systems.

10. An expression system according to claim 8, wherein said first peptide comprises the amino acid sequence of SEQ ID NO: 6.

11. An expression system according to claim 10, wherein said first nucleic acid comprises the nucleotide sequence of SEQ ID NO: 5.

12. An expression system according to claim 8, wherein said second nucleic acid molecule encodes a therapeutic peptide.

13. An expression system according to claim 8, wherein said second nucleic acid molecule encodes a diagnostic peptide.

14. A host cell transformed with the nucleic acid construct according to claim 1.

15. A host cell according to claim 14, wherein said first peptide comprises the amino acid sequence of SEQ ID NO: 8.

16. A host cell according to claim 15, wherein said first nucleic acid comprises the nucleotide sequence of SEQ ID NO:5.

\* \* \* \* \*